US010071039B2

(12) United States Patent
Doi et al.

(10) Patent No.: US 10,071,039 B2
(45) Date of Patent: *Sep. 11, 2018

(54) CLEANSING COMPOSITION FOR SKIN OR HAIR

(71) Applicant: KAO CORPORATION, Tokyo (JP)

(72) Inventors: Yasuhiro Doi, Kainan (JP); Takayuki Nomura, Wakayama (JP)

(73) Assignee: KAO CORPORATION, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 14/416,800

(22) PCT Filed: Sep. 19, 2013

(86) PCT No.: PCT/JP2013/076171

§ 371 (c)(1),
(2) Date: Jan. 23, 2015

(87) PCT Pub. No.: WO2014/046298

PCT Pub. Date: Mar. 27, 2014

(65) Prior Publication Data

US 2015/0174024 A1 Jun. 25, 2015

(30) Foreign Application Priority Data

Sep. 20, 2012 (JP) ................................ 2012-207629
Jun. 25, 2013 (JP) ................................ 2013-133182

(51) Int. Cl.

| | |
|---|---|
| ***A61K 8/46*** | (2006.01) |
| ***A61K 8/92*** | (2006.01) |
| ***A61Q 19/10*** | (2006.01) |
| ***A61Q 5/02*** | (2006.01) |
| ***A61K 8/31*** | (2006.01) |
| ***A61K 8/33*** | (2006.01) |
| ***A61K 8/34*** | (2006.01) |
| ***A61K 8/36*** | (2006.01) |
| ***A61K 8/37*** | (2006.01) |
| ***A61K 8/86*** | (2006.01) |
| ***A61K 8/891*** | (2006.01) |
| ***A61K 8/04*** | (2006.01) |

(52) U.S. Cl.

CPC .............. *A61K 8/466* (2013.01); *A61K 8/046* (2013.01); *A61K 8/31* (2013.01); *A61K 8/33* (2013.01); *A61K 8/342* (2013.01); *A61K 8/361* (2013.01); *A61K 8/375* (2013.01); *A61K 8/86* (2013.01); *A61K 8/891* (2013.01); *A61K 8/92* (2013.01); *A61K 8/922* (2013.01); *A61Q 5/02* (2013.01); *A61Q 19/10* (2013.01); *A61K 2800/592* (2013.01)

(58) Field of Classification Search

None

See application file for complete search history.

(56) References Cited

U.S. PATENT DOCUMENTS

| | | | | |
|---|---|---|---|---|
| 3,332,878 A | | 7/1967 | Coward et al. | |
| 3,708,437 A | | 1/1973 | Sweeney | |
| 3,808,157 A | | 4/1974 | Dewitt et al. | |
| 4,028,283 A | | 6/1977 | Murata et al. | |
| 4,075,129 A | | 2/1978 | Murata et al. | |
| 4,220,548 A | | 9/1980 | Hashimoto et al. | |
| 4,507,223 A | | 3/1985 | Tano et al. | |
| 4,555,351 A | | 11/1985 | Morita et al. | |
| 4,589,988 A | | 5/1986 | Rieck et al. | |
| 4,597,879 A | | 7/1986 | Morita et al. | |
| 4,715,991 A | | 12/1987 | Hirakouchi et al. | |
| 4,852,653 A | | 8/1989 | Borchardt | |
| 4,925,976 A | | 5/1990 | Terao et al. | |
| 5,078,916 A | | 1/1992 | Kok et al. | |
| 5,580,494 A | | 12/1996 | Sandhu et al. | |
| 5,876,705 A | * | 3/1999 | Uchiyama .............. | A61K 8/342 424/70.11 |
| 6,156,297 A | * | 12/2000 | Maurin .................. | A61K 8/463 424/59 |
| 6,184,190 B1 | | 2/2001 | D'Ambrogio et al. | |
| 6,403,654 B1 | * | 6/2002 | De Oliveira ............. | A61K 9/06 424/725 |
| 6,586,379 B1 | | 7/2003 | Seipel | |
| 6,656,454 B1 | | 12/2003 | Koester et al. | |
| 2002/0146442 A1 | | 10/2002 | Sendelbach et al. | |
| 2007/0031362 A1 | | 2/2007 | Kreeger et al. | |
| 2011/0039744 A1 | | 2/2011 | Heath et al. | |
| 2012/0058067 A1 | | 3/2012 | Van Gogh et al. | |
| 2012/0270764 A1 | | 10/2012 | Brown et al. | |
| 2013/0252855 A1 | | 9/2013 | Weerasooriya et al. | |
| 2014/0079658 A1 | | 3/2014 | Terazaki et al. | |
| 2014/0080747 A1 | | 3/2014 | Hirahara et al. | |
| 2015/0202134 A1 | | 7/2015 | Yoshikawa et al. | |

FOREIGN PATENT DOCUMENTS

| | | |
|---|---|---|
| CA | 1338239 C | 4/1996 |
| CN | 86 1 02800 A | 1/1987 |
| EP | 0 377 261 A2 | 7/1990 |
| EP | 0351928 B1 | 6/1993 |
| JP | 49-78706 | 7/1974 |

(Continued)

OTHER PUBLICATIONS

International Search Report and Written Opinion of the International Searching Authority dated Mar. 20, 2013, for International Application No. PCT/JP2013/076176.

(Continued)

*Primary Examiner* — Nicole P Babson
(74) *Attorney, Agent, or Firm* — Birch, Stewart, Kolasch & Birch, LLP

(57) ABSTRACT

Provided is a cleansing composition for skin or hair which can provide a good durability of foam and rinse feel and can enhance the combing property of hair after rinsing and the manageability after drying in application to the hair and can impart a sufficient moist feeling to skin in application to the skin. A cleansing composition for skin or hair, comprising the following (A) and (B): (A) an internal olefin sulfonate having 12 or more and 24 or less carbon atoms; and (B) an oil solution having a solubility of from 0 to 1 g in 100 g of water at 20° C.

24 Claims, No Drawings

(56) References Cited

FOREIGN PATENT DOCUMENTS

| | | | |
|---|---|---|---|
| JP | 54-134711 | A | 10/1979 |
| JP | 55-43138 | A | 3/1980 |
| JP | 55-56196 | A | 4/1980 |
| JP | 56-167799 | A | 12/1981 |
| JP | 59-27995 | A | 2/1984 |
| JP | 59-222466 | A | 12/1984 |
| JP | 61-134366 | A | 6/1986 |
| JP | 1-151510 | A | 6/1989 |
| JP | 1-272564 | A | 10/1989 |
| JP | 2003-81935 | A | 3/2003 |
| JP | 2003-183152 | A | 7/2003 |
| JP | 2006-527785 | A | 12/2006 |
| JP | 2007-15940 | A | 1/2007 |
| JP | 2009-256211 | A | 11/2009 |

OTHER PUBLICATIONS

International Search Report and Written Opinion of the International Searching Authority dated Mar. 20, 2014, for International Application No. PCT/JP2013/076171.

International Search Report and Written Opinion of the International Searching Authority dated Mar. 20, 2014, for International Application No. PCT/JP2013/076172.

International Search Report and Written Opinion of the International Searching Authority dated Mar. 20, 2014, for International Application No. PCT/JP2013/076173.

International Search Report and Written Opinion of the International Searching Authority dated Mar. 20, 2014, for International Application No. PCT/JP2013/076174.

Kosswig et al., "Surfactants", Wiley-VCH Verlag GmbH & Co. KGaA, Weinheim, 2005, XP002554753, pp. 1-76.

U.S. Office Action for U.S. Appl. No. 14/417,079, dated Jan. 25, 2016.

Foster, "Sulfonation and Sulfation Processes," Chemithon, 1997, pp. 1-2.

Suresh et al., "Revisiting Markovnikov Addition to Alkenes via Molecular Electrostatic Potential," J. Org. Chem., vol. 66, No. 21, 2001 (published on web Sep. 18, 2001), pp. 6883-6890.

U.S. Office Action for U.S. Appl. No. 14/417,073, dated Aug. 24, 2017.

KAO Corporation, "KAO AKYPO RLM-45NV", Product Specification for Sodium Laureth-6 Carboxylate, retrieved online on Dec. 6, 2016, 1 page.

Wikihow, "How to Shampoo and Condition Your Hair," https://web.archive.org/web/20090418054258/http://www/wikihow.com/Shampoo-and-C . . . , Apr. 18, 2009, 2 pages.

* cited by examiner

CLEANSING COMPOSITION FOR SKIN OR HAIR

FIELD OF THE INVENTION

The present invention relates to a cleansing composition for skin or hair such as a shampoo and a body shampoo.

BACKGROUND OF THE INVENTION

A cleansing agent is required to have a variety of functions such as emulsifying or cleaning the components of dirt and stains such as oil. Especially, unlike an industrial cleaner, a laundry cleaner, and a house cleaner, it is considered important that a cleansing agent used for skin or hair has not only detergency and excellent foaming performance, but also a favorable durability of foam, rinse feel and a good feel after rinsing and drying. Particularly in the case of hair, good finger combability and softness of the hair after rinsing and drying are desired, and in the case of skin, such an impression is desired that a moist feeling after drying is imparted to the skin washed with a cleansing agent.

Under the foregoing circumstances, olefin sulfonate, which is one of the anionic surfactants, is generally obtained by sulfonating olefin through reactions with gaseous sulfur trioxide-containing gas, followed by neutralization and then hydrolysis of the resulting sulfonic acid. Olefin sulfonate is used in various cleansing agents.

For example, Patent Document 1 discloses a cleansing composition containing a specific internal olefin sulfonate for the purposes of increasing the solubilizing ability, penetrating ability, and interfacial tension reducing ability, and describes that when the above cleansing composition is used as a shampoo, it lathers well without friction, and achieves an improved feel. Also, Patent Document 2 discloses a cleansing composition containing a specific internal olefin sulfonate for the purposes of improving detergency, and describes examples of application to shampoos and the like, and Patent Document 3 also discloses an aqueous liquid cleansing agent containing a specific internal olefin sulfonate and having a low cloud point.

Meanwhile, Patent Document 4 discloses a cleansing composition containing an olefin sulfonate and a low viscosity hydrophobic silicone oil such as octamethyltetrasiloxane or decamethylpentasiloxane for improving the smoothness and silkiness of the hair after drying.

CITATION LIST

Patent Document

[Patent Document 1] JP-A-2003-81935
[Patent Document 2] U.S. Pat. No. 5,078,916
[Patent Document 3] U.S. Pat. No. 3,708,437
[Patent Document 4] JP-A-01-151510

SUMMARY OF THE INVENTION

The present invention provides a cleansing composition for skin or hair, comprising the following (A) and (B) (hereinbelow, may also be referred to as "the cleansing composition of the present invention"):

(A) an internal olefin sulfonate having 12 or more and 24 or less carbon atoms; and (B) an oil solution having a solubility of from 0 to 1 g in 100 g of water at 20° C.

Also, the present invention provides a method for washing hair, comprising applying the aforementioned cleansing composition of the present invention to hair, followed by washing and then rinsing (hereinbelow, may also be referred to as "the method for washing hair according to the present invention").

Further, the present invention provides a method for washing the body, comprising applying the aforementioned cleansing composition of the present invention to a surface of the skin, followed by washing and then rinsing (hereinbelow, may also be referred to as "the method for washing skin according to the present invention").

DETAILED DESCRIPTION OF THE INVENTION

Some cleansing agents for skin or hair may contain various oil solutions such as a silicone oil, an ester oil, and a hydrocarbon oil for improving the feel of use after drying. However, when those oil solutions are used in combination with existing anionic surfactants, sliminess may develop during rinsing and the durability of foam and rinse feel may be deteriorated due to oil solutions mixed therewith, and the combing property of hair after rinsing and the manageability after drying may be deteriorated in application of hair, and further, a moist feeling to the skin after drying tends to be insufficient in application of skin. In view of the above, further improvement is sought for the cleansing agent for skin or hair.

Accordingly, the present invention relates to a cleansing composition for skin or hair capable of bringing about a good durability of foam and rinse feel and, in regard to hair, enhancing the combing property of hair after rinsing and the manageability after drying, and further, in regard to skin, imparting a sufficient moist feeling also to skin.

In light of the above, the present inventors carried out various studies. As a result, they found that a cleansing composition which can impart good combing property after rinsing and the manageability after drying to hair and a sufficient moist feeling also to skin after application, while exhibiting an excellent durability of foam and rinse feel as a cleansing agent for skin or a cleansing agent for hair can be obtained by using a specific internal olefin sulfonate in combination with a specific oil solution.

The cleansing composition of the present invention provides a good durability of foam and rinse feel. In addition, when the cleansing composition is applied to the hair, it gives excellent manageability to the hair after drying while imparting good combing property and softness to hair after rinsing, and when the cleansing composition is applied to skin, it imparts a high moist feeling to the skin. Furthermore, the method for washing hair of the present invention can give excellent manageability to the hair after drying while imparting good combing property and softness to the hair after rinsing. The method for washing skin of the present invention can impart a good moist feeling to the skin.

Hereinbelow, the present invention will be described in detail.

The cleansing composition of the present invention contains the following (A) and (B):

(A) an internal olefin sulfonate having 12 or more and 24 or less carbon atoms; and (B) an oil solution having a solubility of from 0 to 1 g in 100 g of water at 20° C.

The reason is not clear why the cleansing composition of the present invention provides a good durability of foam and rinse feel, the combing property and softness of hair after rinsing, the manageability after drying, and a moist feeling of skin. It is presumed that the internal olefin sulfonate having 12 or more and 24 or less carbon atoms has an appropriate hydrophobicity and thereby shows good compatibility with an oil solution and controls the behavior of the oil solution from cleansing to rinsing. As a result, bubbles are easily broken in a diluted region by rinsing, and washed off, while the oil solution uniformly and effectively remains on the skin or the hair due to adsorption, resulting in improvement in the combing property after rinsing and the manageability after drying of the hair or resulting in improvement in the moist feeling to the skin.

<Internal Olefin Sulfonate (A)>

From the viewpoint of environmental stability, low irritation, and the like, and also from the viewpoint of improving detergency, foam quality, and foamability, and a good durability of foam and rinse feel, and also, imparting the combing property after rinsing and the manageability after drying to hair and a moist feeling to skin, the cleansing composition of the present invention contains an internal olefin sulfonate having 12 or more and 24 or less carbon atoms (hereinbelow, may also be referred to as a component (A)).

In the present invention, an internal olefin sulfonate is an olefin sulfonate obtained by sulfonating an internal olefin (an olefin having a double bond inside the olefin chain) as the raw material, followed by neutralization and then hydrolysis. It should be noted that the above internal olefin has a broad meaning including a trace amount of so-called α-olefin, in which a double bond is present at the C-1 position of the carbon chain. That is, sulfonation of an internal olefin quantitatively produces β-sultone, some of which are converted into γ-sultone and olefin sulfonic acid, which are further converted into hydroxyalkane sulfonate and olefin sulfonate in the process of neutralization and hydrolysis (for example, J. Am. Oil Chem. Soc. 69, 39 (1992)). Here, the hydroxyl group of the hydroxyalkane sulfonate thus obtained is present inside the alkane chain, and the double bond of the olefin sulfonate is present inside the olefin chain. Also, the product thus obtained is mainly a mixture of the aforementioned substances, which may partially contain a trace amount of hydroxyalkane sulfonate having a hydroxyl group at the end of the carbon chain or olefin sulfonate having a double bond at the end of the carbon chain. In the present specification, each of these products and a mixture thereof are collectively referred to as internal olefin sulfonate (component (A)). It should be noted that hydroxyalkane sulfonate is referred to as the hydroxy form of an internal olefin sulfonate (hereinbelow, may also be referred to as HAS), and olefin sulfonate is referred to as the olefin form of an internal olefin sulfonate (hereinbelow, may also be referred to as IOS).

From the viewpoint of improving a durability of foam and rinse feel, and imparting to hair good combing property after rinsing and manageability after drying, and imparting a moist feeling to skin, the number of carbon atoms in the internal olefin sulfonate of the component (A) is 12 or more, preferably 14 or more, and more preferably 16 or more. Also, from the viewpoint of softness of the hair after rinsing, the manageability after drying, and a moist feeling on the skin, the number of carbon atoms in the internal olefin sulfonate of the component (A) is 24 or less, preferably 20 or less, and more preferably 18 or less. Also, from the above viewpoints, the number of carbon atoms in the internal olefin sulfonate of the component (A) is 12 or more and 24 or less, preferably 14 or more and 20 or less, and more preferably 16 or more and 18 or less. These hydroxy form and olefin form containing various numbers of carbon atoms are derived from an internal olefin to be used as the raw material, and a hydroxy form and an olefin form containing different numbers of carbon atoms from those described above may also be contained.

From the viewpoint of improving detergency, foam quality, foamability, durability of foam and rinse feel, and combing property after rinsing and manageability after drying, moist feeling to skin, the content mass ratio (internal olefin sulfonate having 16 carbon atoms/internal olefin sulfonate having 18 carbon atoms) of an internal olefin sulfonate having 16 carbon atoms to an internal olefin sulfonate having 18 carbon atoms in the component (A) or the cleansing composition is preferably from 50/50 to 99/1, more preferably from 60/40 to 95/5, more preferably from 70/30 to 90/10, more preferably from 75/25 to 90/10, more preferably from 75/25 to 85/15, and even more preferably from 78/22 to 85/15.

It is to be noted that the aforementioned mass ratio may be measured by a high-performance liquid chromatograph-mass spectrometer (hereinbelow, abbreviated as HPLC-MS). Specifically, an internal olefin sulfonate having 16 carbon atoms and an internal olefin sulfonate having 18 carbon atoms are separated from the component (A) or the produced cleansing composition by HPLC, each of which may then be identified by analysis with MS, and from the HPLC-MS peak area of each internal olefin sulfonate, the mass ratio between them may be obtained.

From the viewpoint of improving detergency, foam quality, foamability, durability of foam and rinse feel, and combing property after rinsing and manageability after drying, the total content of an internal olefin sulfonate having 16 carbon atoms and an internal olefin sulfonate having 18 carbon atoms in the component (A) is preferably 50% by mass or more, more preferably 60% by mass or more, more preferably 70% by mass or more, more preferably 80% by mass or more, more preferably 90% by mass or more, and even more preferably 95% by mass or more. It should be noted that the upper limit of the aforementioned total content is 100% by mass.

As is apparent from the aforementioned production method, the sulfonate group of the internal olefin sulfonate of the component (A) is present in the carbon chain of an internal olefin sulfonate, namely inside the olefin chain or alkane chain, and the component (A) may partially contain a trace amount of an internal olefin sulfonate having a sulfonate group at the end of the carbon chain. In the present invention, from the viewpoint of foamability, it is preferable that the content of an internal olefin sulfonate in which the sulfonate group is present at the C-2 position of the carbon chain is low, while the content of an internal olefin sulfonate in which the sulfonate group is present further inside is high in the component (A). It should be noted that when the component (A) contains an internal olefin sulfonate having 16 carbon atoms and an internal olefin sulfonate having 18 carbon atoms, it is more preferable that the content of an internal olefin sulfonate in which the sulfonate group is present at the C-2 position of the carbon chain is low, with respect to both of the above internal olefin sulfonates having 16 and 18 carbon atoms.

From the viewpoint of improving lathering property, foam quality, and a rinse feel as well as imparting the good combing property after rinsing and the manageability after drying to hair and a moist feeling to skin, the content of an internal olefin sulfonate in which the sulfonate group is present at the C-2 position in the component (A) is preferably 25% by mass or less, more preferably 24% by mass or less, more preferably 23% by mass or less, more preferably 22% by mass or less, preferably 20% by mass or less, more preferably less than 20% by mass, more preferably 19% by mass or less, and even more preferably 18% by mass or less. Also, from the viewpoint of rinse feel and combing property, the content of an internal olefin sulfonate in which the sulfonate group is present at the C-2 position in the component (A) is preferably 17.5% by mass or less, more preferably 15% by mass or less, more preferably 12% by mass or less, and even more preferably 10% by mass or less. Also, from the viewpoint of reducing the production cost and improving productivity and from the viewpoint of durability of foam and manageability, the lower limit of the content of an internal olefin sulfonate in which the sulfonate group is present at the C-2 position in the component (A) is preferably 5% by mass or more, more preferably 6% by mass or more, more preferably 7% by mass or more, and even more preferably 8% by mass or more. Also, from the viewpoint of durability of foam, manageability, moist feeling to skin, the lower limit of the content of an internal olefin sulfonate in which the sulfonate group is present at the C-2 position in the component (A) is preferably 9% by mass or more, more preferably 10% by mass or more, more preferably 12% by mass or more, more preferably 14% by mass or more, and even more preferably 16% by mass or more. Further, from the above viewpoints, the content of an internal olefin sulfonate in which the sulfonate group is present at the C-2 position in the component (A) is preferably 5% by mass or more and 25% by mass or less, more preferably 5% by mass or more and 24% by mass or less, more preferably 5% by mass or more and 23% by mass or less, more preferably 5% by mass or more and 22% by mass or less, preferably 5% by mass or more and 20% by mass or less, more preferably 6% by mass or more and less than 20% by mass, more preferably 7% by mass or more and 19% by mass or less, and even more preferably 8% by mass or more and 18% by mass or less.

Also, from the viewpoint of rinse feel and combing property, the content of an internal olefin sulfonate in which the sulfonate group is present at the C-2 position in the component (A) is preferably 9% by mass or more and 17.5% by mass or less, more preferably 9% by mass or more and 15% by mass or less, more preferably 9% by mass or more and 12% by mass or less, and even more preferably 9% by mass or more and 10% by mass or less. Also, from the viewpoint of durability of foam, manageability, moist feeling to skin, the content of an internal olefin sulfonate in which the sulfonate group is present at the C-2 position in the component (A) is preferably 9% by mass or more and 18% by mass or less, more preferably 10% by mass or more and 18% by mass or less, more preferably 12% by mass or more and 18% by mass or less, more preferably 14% by mass or more and 18% by mass or less, and even more preferably 16% by mass or more and 18% by mass or less.

It should note that the content of an internal olefin sulfonate in which the sulfonate group is present at the C-2 position in the component (A) may be measured by a method such as nuclear magnetic resonance spectroscopy. More specifically, it may be measured by a method using gas chromatography described later in Example.

Also, from the viewpoint of improving lathering property, foam quality, and a rinse feel as well as imparting the good combing property after rinsing and the manageability after drying to hair, and a moist feeling to skin, the content of an olefin sulfonate in which the sulfonate group is present at the C-1 position of the olefin chain or alkane chain in the component (A) is preferably 3.0% by mass or less, more preferably 2.5% by mass or less, more preferably 2.0% by mass or less, more preferably 1.5% by mass or less, and even more preferably 1.0% by mass or less, and from the viewpoint of reducing the production cost and improving productivity, the lower limit of the aforementioned content is preferably 0.01% by mass or more.

Further, from the viewpoint of improving lathering property, foam quality, and a rinse feel as well as imparting the good combing property after rinsing and the manageability after drying to hair, and a moist feeling to skin, the content of an internal olefin sulfonate in which the sulfonate group is present further inside than the C-3 position of the olefin chain or alkane chain in the component (A) is preferably 70% by mass or more, more preferably 75% by mass or more, and even more preferably 80% by mass or more.

The internal olefin sulfonate is preferably a mixture of the hydroxy form and the olefin form. From the viewpoint of improving productivity and reducing impurities, the content mass ratio (hydroxy form/olefin form) of the hydroxy form of an internal olefin sulfonate to the olefin form of an internal olefin sulfonate in the component (A) or the cleansing composition is preferably from 50/50 to 100/0, more preferably from 60/40 to 100/0, more preferably from 70/30 to 100/0, more preferably from 75/25 to 100/0, and even more preferably from 75/25 to 95/5.

The mass content ratio of the hydroxy form of an internal olefin sulfonate to the olefin form of an internal olefin sulfonate in the component (A) or the cleansing composition according to the present invention may be obtained by separating the hydroxy form and the olefin form from the component (A) or the produced cleansing composition by HPLC and then measuring the separated substances by the method described in Examples.

From the viewpoint of improving the durability of foam and rinse feel, and imparting the combing property to hair and a moist feeling to skin, the content of the aforementioned component (A) in the cleansing composition of the present invention is preferably 0.1% by mass or more, more preferably 1% by mass or more, more preferably 2% by mass or more, more preferably 5% by mass or more, more preferably 7% by mass or more, and even more preferably 10% by mass or more, from the viewpoint of improving manageability of hair after drying, and also from the viewpoint of improving rinse feel and imparting the combing property to hair and a moist feeling to skin, the content of the aforementioned component (A) in the cleansing composition of the present invention is preferably 80% by mass or less, more preferably 50% by mass or less, more preferably 30% by mass or less, more preferably 20% by mass or less, more preferably 16% by mass or less, and even more preferably 14% by mass or less. Also, from the above viewpoints, the content of the aforementioned component (A) in the cleansing composition of the present invention is preferably 0.1% by mass or more and 80% by mass or less, more preferably 1% by mass or more and 50% by mass or less, more preferably 2% by mass or more and 30% by mass or less, more preferably 5% by mass or more and 20% by mass or less, more preferably 7% by mass or more and 16% by mass or less, and even more preferably 10% by mass or more and 14% by mass or less.

The internal olefin sulfonate (A) is obtainable by sulfonating a raw material internal olefin having 12 or more and 24 or less carbon atoms, followed by neutralization and then hydrolysis. No particular limitation is imposed on the conditions of sulfonation, neutralization, and hydrolysis, and for example, the conditions described in U.S. Pat. Nos. 1,633,184 and 2,625,150, and Tenside Surf. Det. 31 (5) 299 (1994) may be referred to.

As mentioned above, in the present invention, a raw material internal olefin refers to an olefin substantially having a double bond inside the olefin chain. From the viewpoint of improving the lathering property, durability of foam and rinse feel of the cleansing composition, and imparting the combing property of the hair after rinsing and a moist feeling to skin, the number of carbon atoms in the raw material internal olefin is preferably from 12 to 24, more preferably from 12 to 20, more preferably from 12 to 18, more preferably from 14 to 18, and even more preferably from 16 to 18. An internal olefin to be used as the raw material may be used singly or a combination of two or more thereof may be used.

From the viewpoint of acquiring lathering property and a creamy foam quality for easy washing, improving rinse feel, acquiring a good feel (combing property) after rinsing, and also from the viewpoint of imparting manageability to hair and a moist feeling to skin, a content of an internal olefin in which the double bond is present at the C-2 position in the raw material internal olefin is preferably 40% by mass or less, more preferably 35% by mass or less, more preferably 32% by mass or less, more preferably 30% by mass or less, more preferably 27% by mass or less, and also, from the viewpoint of rinse feel and combing property, more preferably 25% by mass or less, more preferably 20% by mass or less, more preferably less than 20% by mass, more preferably 19% by mass or less, and even more preferably 18% by mass or less. Also, from the viewpoint of reducing the production cost and improving productivity, and durability of foam and manageability, the lower limit of the aforementioned content is preferably 5% by mass or more, more preferably 6% by mass or more, more preferably 7% by mass or more, more preferably 8% by mass or more, more preferably 9% by mass or more, more preferably 12% by mass or more, and even more preferably 15% by mass or more, and also from the viewpoint of durability of foam, manageability, moist feeling to skin, more preferably 20% by mass or more, more preferably 22% by mass or more, and even more preferably 24% by mass or more.

Also, from the above viewpoints, the content of an internal olefin in which the double bond is present at the C-2 position in the raw material internal olefin is preferably 5% by mass or more and 40% by mass or less, more preferably 5% by mass or more and 35% by mass or less, more preferably 5% by mass or more and 32% by mass or less, more preferably 5% by mass or more and 30% by mass or less, preferably 6% by mass or more and 30% by mass or less, more preferably 7% by mass or more and 30% by mass or less, more preferably 8% by mass or more and 30% by mass or less, more preferably 9% by mass or more and 30% by mass or less, more preferably 12% by mass or more and 30% by mass or less, and even more preferably 15% by mass or more and 27% by mass or less. Further, from the viewpoint of rinse feel and combing property, a content of an internal olefin in which the double bond is present at the C-2 position in the raw material internal olefin is preferably 15% by mass or more and 25% by mass or less, more preferably 15% by mass or more and 20% by mass or less, more preferably 15% by mass or more and less than 20% by mass, more preferably 15% by mass or more and 19% by mass or less, and even more preferably 15% by mass or more and 18% by mass or less. Also, from the viewpoint of durability of foam, manageability, moist feeling to skin, a content of an internal olefin in which the double bond is present at the C-2 position in the raw material internal olefin is preferably 20% by mass or more and 27% by mass or less, more preferably 22% by mass or more and 27% by mass or less, and even more preferably 24% by mass or more and 27% by mass or less.

Also, from the viewpoint of improving lathering property, foam quality, and a rinse feel as well as imparting the good combing property after rinsing and the manageability after drying to hair, and a moist feeling to skin, the content of an olefin in which the double bond is present at the C-1 position, namely a olefin, in the raw material internal olefin is preferably 3.0% by mass or less, more preferably 2.5% by mass or less, more preferably 2.0% by mass or less, more preferably 1.5% by mass or less, and even more preferably 1.0% by mass or less, and from the viewpoint of reducing the production cost and improving productivity, the lower limit of the aforementioned content is preferably 0.01% by mass or more.

Further, from the viewpoint of improving lathering property, foam quality, and a rinse feel as well as imparting the good combing property after rinsing and the manageability after drying to hair, and a moist feeling to skin, the total content of a raw material internal olefin in which the double bond is present further inside than the C-3 position in the raw material internal olefin is preferably 65% by mass or more, more preferably 70% by mass or more, more preferably 75% by mass or more, and even more preferably 80% by mass or more.

The distribution of the double bond in the raw material internal olefin may be measured by a method described in Examples using a gas chromatograph mass spectrometer (hereinbelow, abbreviated as GC-MS). Specifically, components each having different carbon chain lengths and double bond positions are accurately separated by a gas chromatograph analyzer (hereinbelow, abbreviated as GC), and each component is then analyzed by a mass spectrometer (hereinbelow, abbreviated as MS) to identify the position of double bond, and from the resulting GC peak area, the fraction of each component may be found out.

The aforementioned sulfonation reaction may be carried out by reacting a sulfur trioxide gas with an internal olefin at a ratio of from 1.0 to 1.2 moles of sulfur trioxide per mole of the raw material internal olefin. The reactions are preferably carried out at a reaction temperature of from 20 to 40° C.

Neutralization is carried out by reacting from 1.0 to 1.5 times the molar amount of an alkaline aqueous solution such as sodium hydroxide, ammonia, or 2-aminoethanol with the theoretical value of sulfonate group.

The hydrolysis reaction may be carried out at from 90 to 200° C. for from 30 minutes to three hours in the presence of water. These reactions may be successively carried out. Also, upon completion of the reactions, the products may be purified by extraction, washing, and the like.

Also, in the production of the internal olefin sulfonate (A), the raw material internal olefin in which the number of carbon atoms is distributed in from 12 to 24 may be subjected to sulfonation, neutralization, and hydrolysis, or the raw material internal olefin having a uniform number of carbon atoms may be subjected to sulfonation, neutralization, and hydrolysis. Also, a plurality of internal olefin sulfonates each having different numbers of carbon atoms may be produced in advance and then mixed, as needed.

As the internal olefin sulfonate composition (A) of the present invention is obtained by sulfonating an internal olefin, followed by neutralization and hydrolysis as described above, an unreacted raw material internal olefin and inorganic compounds may remain in the composition (A). It is preferred that the contents of these components are much smaller.

The content of the raw material internal olefin in the component (A) of the present invention is preferably less than 5.0% by mass, more preferably less than 3.0% by mass, more preferably less than 1.5% by mass, and even more preferably less than 1.0% by mass in the component (A), from the viewpoint of improving durability of foam and rinse feel, and imparting to hair good combing property and softness after rinsing and imparting moist feeling to skin.

The content of the unreacted internal olefin may be measured by a method described later in Examples.

The content of the inorganic compounds in the component (A) of the present invention is preferably less than 7.5% by mass, more preferably less than 5.0% by mass, more preferably less than 3.0% by mass, more preferably less than 2.0% by mass, and even more preferably less than 1.6% by mass in the component (A), from the viewpoint of improving durability of foam and rinse feel, and imparting to hair good combing property and softness after rinsing and imparting moist feeling to skin.

In this context, the inorganic compounds include sulfates and alkali agents. The content of these inorganic compounds may be measured by a potentiometric titration. Specifically, the content may be measured by a method described later in Examples.

<Oil Solution (B)>

The cleansing composition of the present invention comprises an oil solution having a solubility of from 0 to 1 g in 100 g of water at 20° C. (hereinafter, referred to as component (B)) from the viewpoints of improving the durability of foam and rinse feel and imparting combing property to the hair or a moist feeling to the skin.

The oil agent (B) used in the present invention may be any hardly water-soluble or water-insoluble oil solution having a solubility of from 0 to 1 g in 100 g of water at 20° C., that is used as an oil ingredient in pharmaceutical products, quasi-drugs, cosmetics, toiletries, and other general merchandise, and the like.

Examples of oil solution (B) having a solubility of from 0 to 1 g in 100 g of water at 20° C. include an ester oil, a silicone oil, an ether oil, a hydrocarbon oil, a higher alcohol, and carboxylic acid having a hydrocarbon group having from 17 to 23 carbon atoms which may be substituted by a hydroxyl group. Among these oils, one or two or more selected from the ester oil, silicone oil, ether oil, hydrocarbon oil, higher alcohol, and carboxylic acid having a hydrocarbon group having from 17 to 23 carbon atoms which may be substituted by a hydroxyl group are preferably used. More preferably, the ester oil, silicone oil, ether oil, hydrocarbon oil, or higher alcohols is used; and even more preferably, the ester oil, silicone oil, ether oil, or higher alcohol is used. These oils may be used alone or in combination of two or more thereof.

The ester oil is preferably one represented by Formula (1) or (2) shown below or a hydrophobic carboxylic acid ester of dipentaerythritol, from the viewpoint of imparting good manageability to hair after drying when the hair is treated with the cleansing composition of the present invention and the viewpoint of imparting a moist feeling to skin when the cleansing composition is applied to the body.

$$R'—COO—R^2 \quad (1)$$

(wherein $R^1$ represents a linear or branched alkyl or alkenyl group having from 8 to 22 carbon atoms; and $R^2$ represents a linear or branched alkyl or alkenyl group having from 1 to 22 carbon atoms.)

In Formula (1), the number of carbon atoms of $R^1$ is preferably from 10 to 20 and more preferably from 12 to 18 from the viewpoints of improving the durability of foam and rinse feel as well as manageability of the hair. From the same viewpoints, the number of carbon atoms of $R^2$ is preferably from 1 to 20 and more preferably from 1 to 18. $R^2$ is even more preferably a linear or branched alkyl or alkenyl group having from 1 to 18 carbon atoms, which may be interrupted by a propyleneoxy group or a phenyl group.

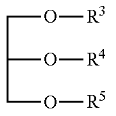

(2)

(wherein $R^3$, $R^4$, and $R^5$ each independently represent a hydrogen atom or a group represented by Formula (3), provided that they are not simultaneously hydrogen atoms.)

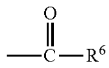

(3)

(wherein $R^6$ represents a linear or branched alkyl or alkenyl group having from 8 to 22 carbon atoms which may be substituted by a hydroxyl group).

In Formula (3), the number of carbon atoms of $R^6$ is preferably from 8 to 20, more preferably from 8 to 18, more preferably from 14 to 18, and even more preferably from 16 to 18 from the viewpoints of improving the durability of foam and rinse feel as well as the manageability of the hair.

Specific examples of the ester oil represented by Formula (1) or (2) include castor oil, cacao oil, mink oil, avocado oil, olive oil, sunflower oil, *camellia* oil, apricot kernel oil, almond oil, wheat germ oil, *theobroma grandiflorum* seed oil, grape seed oil, babassu oil, jojoba oil, macadamia nut oil, *camellia oleifera* seed oil, shea butter oil, *camellia reticulata* seed oil, meadowfoam oil, bees wax, lanolin, hydrogenated lanolin, octyldodecyl lanolate, caprylyl eicosenoate, myristyl 2-ethylhexanoate, cetyl 2-ethylhexanoate, stearyl 2-ethylhexanoate, octyl octanoate, lauryl octanoate, myristyl octanoate, isocetyl octanoate, octyl propylheptanoate, cetostearyl isononanoate, isononyl isononanoate, isotridecyl isononanoate, methyl laurate, hexyl laurate, octyl laurate, isopropyl myristate, octyl myristate, myristyl myristate, octyldodecyl myristate, isopropyl palmitate, 2-ethylhexyl palmitate, octyl palmitate, cetyl palmitate, methyl oleate, oleyl oleate, decyl oleate, isobutyl oleate, methyl stearate, 2-ethylhexyl stearate, octyl stearate, isocetyl stearate, stearyl stearate, butyl stearate, isotridecyl stearate, isopropyl isostearate, isocetyl isostearate, isostearyl isostearate, propylene glycol isostearate, 2-ethylhexyl hydroxystearate, oleyl erucate, 2-ethylhexyl succinate, sucrose polysoyate, sucrose polybehenate, sucrose tetraisostearate, glyceryl tribehenate, and triisostearin, and the like. Examples of other ester oil include diisopropyl dimerate, propanediol dicaprate, diisopropyl adipate, diethoxyethyl succinate, hydroxyalkyl (C16-18) hydroxydimer dilinoleyl ether, and pentaerythrityl tetrastearate, and the like.

Among them, from the viewpoint of imparting good manageability after drying to hair when the cleansing composition of the present invention is applied to hair and imparting a moist feeling to the skin when the cleansing composition of the present invention is applied to the body, jojoba oil, glyceryl isostearate, sunflower oil, avocado oil, *camellia* oil, macadamia nut oil, shea butter oil, octyl laurate, octyl myristate, octyldodecyl myristate, isopropyl myristate, myristyl myristate, isopropyl palmitate, 2-ethylhexyl palmitate, octyl palmitate, cetyl palmitate, methyl stearate, 2-ethylhexyl stearate, octyl stearate, isocetyl stearate, stearyl stearate, butyl stearate, or isotridecyl stearate is preferable, and one or two or more selected from jojoba oil, glyceryl isostearate, octyldodecyl myristate, sunflower oil, avocado oil, *camellia* oil, macadamia nut oil, shea butter oil, octyl laurate, octyl myristate, myristyl myristate, isopropyl palmitate, octyl palmitate, cetyl palmitate, octyl stearate, isocetyl stearate, stearyl stearate, isostearyl stearate, and isostearyl isostearate are more preferable.

The hydrophobic carboxylic acid ester of dipentaerythritol refers to a compound obtained by subjecting dipentaerythritol to dehydration condensation with one or more hydrophobic carboxylic acids. Here, the hydrophobic carboxylic acid refers to a carboxylic acid having a hydrocarbon group having from 16 to 24 carbon atoms optionally having a hydroxyl group. Specific examples of the hydrophobic carboxylic acid include palmitic acid, stearic acid, oleic acid, isostearic acid, hydroxystearic acid, or rosin acid. Among them, from the viewpoint of availability, an ester of mixed acid of hydroxystearic acid, stearic acid, and rosin acid and dipentaerythritol is preferable.

From the viewpoint of imparting good manageability after drying to hair when the cleansing composition of the present invention is applied to hair and imparting a moist feeling to the skin when the cleansing composition of the present invention is applied to the body, as the aforementioned silicone oil, one or two or more selected from dimethylpolysiloxane, dimethiconol (dimethylpolysiloxane having a hydroxyl group at the end), and amino modified silicone (dimethylpolysiloxane having an amino group within the molecule), polyether modified silicone, glyceryl modified silicone, amino derivative silicone, silicone wax, and silicone elastomer are preferable.

The silicone oil preferably has a viscosity of from 10 to 15,000,000 $mm^2/s$ from the viewpoint of imparting good finger combability and manageability to hair when the cleansing composition of the present invention is applied to the hair, the viewpoint of imparting a moist feeling to skin when the cleansing composition is applied to the body, and the viewpoint of dispersibility in the preparation of the cleansing composition.

The ether oil is preferably one represented by Formula (4) shown below from the viewpoint of improving the durability of foam and rinse feel of the cleansing composition of the present invention, from the viewpoint of imparting good manageability to hair after drying when the hair is treated with the cleansing composition, as well as from the viewpoint of imparting a moist feeling to skin when the cleansing composition is applied to the body.

$$R^7—O—(PO)_r(EO)_s—R^8 \quad (4)$$

(wherein $R^7$ represents a linear or branched alkyl or alkenyl group having from 6 to 22 carbon atoms; $R^8$ represents a hydrogen atom or a linear or branched alkyl or alkenyl group having from 1 to 16 carbon atoms; PO represents a propyleneoxy group; EO represents an ethyleneoxy group; r represents an average mole number of PO added and is a number of from 0.1 to 15; s represents an average mole number of EO added and is a number of from 0 to 10; and when s is not 0, PO and EO may be added in a random or block form, and the order in which PO and EO are added is not limited).

In Formula (4), the number of carbon atoms of $R^7$ is preferably from 6 to 20, more preferably from 6 to 18, and even more preferably from 8 to 18; $R^8$ is preferably a hydrogen atom, or the number of carbon atoms of $R^8$ is preferably from 1 to 12 carbon atoms and more preferably from 1 to 8 carbon atoms; and the average mole number r of PO added is preferably from 1 to 15 and more preferably from 2 to 13, from the viewpoint of improving the durability of foam and rinse feel of the cleansing composition of the present invention, from the viewpoint of imparting good manageability to hair after drying when the hair is treated with the cleansing composition, as well as from the viewpoint of imparting a moist feeling to skin when the cleansing composition is applied to the body.

Specific examples of the aforementioned ether oil preferably include polyoxypropylene hexyl ether, polyoxypropylene octyl ether, polyoxypropylene decyl ether, polyoxypropylene lauryl ether, dihexyl ether, dioctyl ether, didecyl ether, dilauryl ether, dimyristyl ether, dicetyl ether, distearyl ether, diicosyl ether, and dibehenyl ether, in which the average number of moles of propyleneoxy groups added is from 1 to 15, more preferably from 2 to 10.

Among them, from the viewpoint of improving a durability of foam and rinse feel and the feel of the cleansing composition of the present invention, polyoxypropylene hexyl ether, polyoxypropylene octyl ether, polyoxypropylene decyl ether, polyoxypropylene lauryl ether, dioctyl ether, didecyl ether, and dilauryl ether in which the average number of moles of oxypropylene added is from 1 to 5, more preferably from 2 to 4, and even more preferably 3 are preferable, and one or two or more selected from polyoxypropylene octyl ether, polyoxypropylene decyl ether, and polyoxypropylene lauryl ether in which the average number of moles of oxypropylene added is from 1 to 5, more preferably from 2 to 4, and even more preferably 3 are more preferable.

From the viewpoint of improving the durability of foam and rinse feel, and imparting good manageability after drying when the cleansing composition of the present invention is applied to the hair, and imparting a moist feeling to the skin when the cleansing composition of the present invention is applied to the body, the aforementioned hydrocarbon oil is preferably saturated or unsaturated hydrocarbon having 20 or more carbon atoms.

Specific examples of the aforementioned hydrocarbon oil include squalene, squalane, liquid paraffin, liquid isoparaffin, heavy liquid isoparaffin, α-olefin oligomer, cycloparaffin, polybutene, petroleum jelly, paraffin wax, microcrystalline wax, polyethylene wax, or ceresin. From the viewpoint of imparting good manageability to hair when the cleansing composition of the present invention is applied, petroleum jelly, squalane, squalene, liquid paraffin, or paraffin wax is preferable, and one or two or more selected from petroleum jelly, squalane, liquid paraffin, and paraffin wax are more preferable.

From the viewpoint of imparting good manageability after drying to hair and imparting a moist feeling to the skin when the cleansing composition of the present invention is applied to the body, the aforementioned higher alcohol is preferably an alcohol having a linear or branched alkyl group or alkenyl group having from 6 to 22 carbon atoms. The number of carbon atoms in the above alkyl group or alkenyl group is more preferably from 8 to 20, and even more preferably from 12 to 18.

Specific examples of the aforementioned higher alcohol include hexyl alcohol, 2-ethylhexyl alcohol, octyl alcohol, decyl alcohol, isodecyl alcohol, lauryl alcohol, myristyl alcohol, palmityl alcohol, cetyl alcohol, stearyl alcohol, isostearyl alcohol, 2-octyl dodecanol, icosyl alcohol, or behenyl alcohol.

Among them, from the viewpoint of providing lathering property and foam quality for easy washing according to the cleansing composition of the present invention, imparting good manageability after drying to hair when the cleansing composition of the present invention is applied, and imparting a moist feeling to the skin when the cleansing composition of the present invention is applied to the body, lauryl alcohol, myristyl alcohol, cetyl alcohol, stearyl alcohol, behenyl alcohol, or 2-octyl dodecanol is preferable, of which lauryl alcohol, myristyl alcohol, cetyl alcohol, stearyl alcohol, or 2-octyl dodecanol is more preferable, and one or two or more selected from myristyl alcohol, cetyl alcohol, stearyl alcohol, and 2-octyl dodecanol are more preferable.

The hydrocarbon group of the aforementioned carboxylic acid having a hydrocarbon group having from 17 to 23 carbon atoms which may be substituted by a hydroxyl group is preferably a linear or branched alkyl group or alkenyl group.

Specific examples of the carboxylic acid having a hydrocarbon group having from 17 to 23 carbon atoms which may be substituted by a hydroxyl group include stearic acid, oleic acid, isostearic acid, hydroxystearic acid, behenic acid, or rosin acid. Among them, from the viewpoint of imparting good manageability after drying to hair when the cleansing composition of the present invention is applied and imparting a moist feeling to the skin when the cleansing composition of the present invention is applied to the body, stearic acid, oleic acid, isostearic acid, hydroxystearic acid, or behenic acid is preferable, of which oleic acid or isostearic acid is more preferable.

From the viewpoint of imparting good manageability after drying to hair when the cleansing composition of the present invention is applied to the hair and imparting a moist feeling to the skin when the cleansing composition of the present invention is applied to the body, the solubility of the aforementioned component (B) to be used in the present invention in 100 g of water of 20° C. is from 0 to 1 g, preferably from 0 to 0.5 g, and more preferably from 0 to 0.1 g.

The content of the component (B) is preferably 0.01% by mass or more, more preferably 0.03% by mass or more, more preferably 0.05% by mass or more, more preferably 0.1% by mass or more, and even more preferably 0.5% by mass or more in the cleansing composition of the present invention, from the viewpoint of imparting good manageability to hair after drying when the hair is treated with the cleansing composition and the viewpoint of imparting a moist feeling to skin when the cleansing composition is applied to the body. The content of the component (B) is preferably 30% by mass or less, more preferably 20% by mass or less, more preferably 15% by mass or less, more preferably 10% by mass or less, more preferably 5% by mass or less, and even more preferably 2% by mass or less from the viewpoint of improving the durability of foam and rinse feel of the cleansing composition of the present invention. The content of the component (B) is preferably from 0.01 to 30% by mass, more preferably from 0.03 to 20% by mass, more preferably from 0.05 to 15% by mass, more preferably from 0.1 to 10% by mass, more preferably from 0.5 to 5% by mass, and even more preferably 0.5 to 2% by mass from the above viewpoints.

When the cleansing composition of the present invention is for hair, the content of the oil solution (B) is more preferably from 0.1 to 10% by mass, more preferably from 0.5 to 8% by mass, more preferably from 0.5 to 5% by mass, and even more preferably 0.5 to 2% by mass in the cleansing composition of the present invention, from the viewpoints of the durability of foam and rinse feel and the good manageability of hair after drying when the hair is treated with the cleansing agent. When the cleansing composition of the present invention is for skin, the content of the component (B) is more preferably from 0.1 to 20% by mass, more preferably from 1 to 10% by mass, more preferably from 0.5 to 5% by mass, and even more preferably 0.5 to 2% by mass in the cleansing composition of the present invention, from the viewpoints of the improving durability of foam and rinse feel and imparting a moist feeling to skin.

The mass content ratio of the component (A) to the component (B) [component (A)/component (B)] is preferably from 0.2 to 1000, more preferably from 0.5 to 200, more preferably from 1 to 100, more preferably from 5 to 50, more preferably from 8 to 20, and even more preferably 10 to 15 from the viewpoint of imparting good manageability to hair after drying when the hair is treated with the cleansing composition of the present invention and the viewpoint of imparting a moist feeling to skin when the cleansing composition is applied to the body.

The cleansing composition of the present invention may contain a surfactant (hereinafter, also referred to as component (C)) other than the component (A) as long as the effects of the present invention is not impaired.

The surfactant other than the component (A) may be any surfactant which is usually used in pharmaceutical products, quasi-drugs, cosmetics, toiletries, and other general merchandise, and the like, and specific examples thereof include anionic surfactants, nonionic surfactants, amphoteric surfactants, and cationic surfactants, excluding those used as the component (A). In particular, the surfactant other than the component (A) is preferably an anionic surfactant or an amphoteric surfactant other than the component (A) from the viewpoints of improvements in detergency, foamability, and foam quality.

The anionic surfactant other than the component (A) is preferably a sulfuric acid ester salt, a sulfonate, a carboxylate, a phosphoric acid ester salt, or an amino acid salt, from the viewpoints of detergency, foamability, and foam quality. Specific examples of the anionic surfactant include sulfuric acid ester salts such as alkyl sulfates, alkenyl sulfates, polyoxyalkylene alkyl ether sulfates, polyoxyalkylene alkenyl ether sulfates, and polyoxyalkylene alkylphenyl ether sulfates; sulfonates such as sulfosuccinic acid alkyl ester salt, polyoxyalkylene sulfosuccinic acid alkyl ester salt, alkane sulfonates, acyl isethionates, and acyl methyl taurates; higher fatty acid salts having from 8 to 16 carbon atoms; phosphoric acid ester salts such as alkyl phosphates and polyoxyalkylene alkyl ether phosphates; and amino acid salts such as acyl glutamates, alanine derivatives, glycine derivatives, and arginine derivatives, and the like.

The anionic surfactant preferably has an alkyl or alkenyl group having from 8 to 20 carbon atoms and more preferably an alkyl or alkenyl group having from 10 to 16 carbon atoms, from the viewpoints of detergency, foamability, and foam quality and from the viewpoint of imparting good manageability to hair after drying when the hair is treated with the cleansing composition of the present invention and the viewpoint of imparting a moist feeling to skin when the cleansing composition is applied to the body.

Examples of the nonionic surfactant include polyethylene glycol type nonionic surfactants such as polyoxyethylene sorbitan fatty acid esters, polyoxyethylene sorbit fatty acid esters, polyoxyethylene glycerin fatty acid esters, polyoxyethylene fatty acid esters, polyoxyethylene alkyl ethers, polyoxyethylene alkylphenyl ethers, and polyoxyalkylene (hydrogenated) castor oil; polyhydric alcohol type nonionic surfactants such as sucrose fatty acid esters, polyglycerol alkyl ethers, polyglycerol fatty acid esters, and alkyl glycosides; and fatty acid alkanolamides.

The nonionic surfactant having an alkyl or alkenyl group having from 8 to 20 carbon atoms as the hydrophobic site is preferred from the viewpoints of detergency of the cleansing composition of the present invention and volume of foam and foam quality during washing and from the viewpoint of imparting good manageability to hair after drying when the hair is treated with the cleansing composition of the present invention.

Among them, alkyl glucosides having from 8 to 18 and preferably from 8 to 12 carbon atoms such as decyl glucoside; polyoxyethylene alkyl ethers such as polyoxyethylene lauryl ether; and fatty acid monoalkanolamides such as coconut oil fatty acid monoethanolamide are preferred; and decyl glucoside, polyoxyethylene(3) lauryl ether (laureth-3), polyoxyethylene(16) myristyl ether (steareth-16), coconut oil fatty acid monoethanolamide, and coconut oil fatty acid N-methyl monoethanolamide are more preferred.

Examples of the amphoteric surfactant include betaine surfactants such as imidazoline betaine, betaine alkyldimethyl aminoacetate, fatty acid amide propylbetaine, and sulfobetaine; and amine oxide surfactants such as alkyl dimethylamine oxide, and the like.

In particular, from the viewpoints of detergency of the cleansing composition of the present invention and volume of foam and foam quality during washing and from the viewpoint of imparting good manageability to hair after drying when the hair is treated with the cleansing composition of the present invention, imidazoline betaine, sulfobetaine, and fatty acid amide propylbetaine, and the like are preferred; and specifically, coconut oil fatty acid amide propyl betaine, lauryl carbomethoxy methylhydroxy imidazolium betaine, betaine dimethylaminoacetate, or lauryl hydroxy sulfobetaine are more preferred.

Examples of the cationic surfactant include mineral acid and organic acid salts of tertiary amines represented by Formula (5) shown below and quaternary ammonium salt surfactants represented by Formula (6) shown below.

(5)

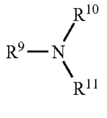

(wherein $R^9$ represents a linear or branched alkyl or alkenyl group having from 6 to 28 carbon atoms, which may be interrupted by an amide group, an ester group, or an ether group; $R^{10}$ represents a linear or branched alkyl, alkenyl, or alkanol group having from 1 to 28 carbon atoms, which may be interrupted by an amide group, an ester group, or an ether group; and $R^{11}$ represents a linear or branched alkyl or alkanol group having from 1 to 3 carbon atoms.)

In Formula (5), the number of carbon atoms of $R^9$ is preferably from 12 to 28, more preferably from 14 to 25, and even more preferably from 16 to 25, from the viewpoint of improving the combing property after rinsing when the cleansing composition of the present invention is applied to hair and the viewpoint of imparting good manageability to hair after drying. From the same viewpoints, the number of carbon atoms of $R^{10}$ is preferably from 12 to 28, more preferably from 14 to 25, and even more preferably from 16 to 25 and is preferably a methyl group, an ethyl group, or a hydroxylethyl group. From the same viewpoints, $R^{11}$ is preferably a methyl group, an ethyl group, or a hydroxylethyl group.

The mineral acid and the organic acid which form salts with the tertiary amine represented by Formula (5) are not particularly limited, and hydrogen halides, sulfuric acid, acetic acid, citric acid, lactic acid, glutamic acid, and alkyl sulfuric acid having 1 to 3 carbon atoms are preferred from the viewpoint of dispersion stability of the surfactant. The hydrogen halide is preferably hydrogen chloride from the viewpoint of chemical stability.

(6)

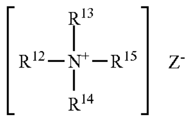

(wherein $R^{12}$ represents a linear or branched alkyl or alkenyl group having from 6 to 28 carbon atoms, which may be interrupted by an amide group, an ester group, or an ether group; $R^{13}$ represents a linear or branched alkyl, alkenyl, or alkanol group having from 1 to 28 carbon atoms, which may be interrupted by an amide group, an ester group, or an ether group; $R^{14}$ and $R^{15}$ each represent a linear or branched alkyl group having from 1 to 3 carbon atoms; and $Z^-$ represents an anionic group as the counter ion of the ammonium salt.)

In Formula (6), a preferred embodiment of $R^{12}$ is the same as the preferred embodiment of $R^9$ in Formula (5), from the viewpoint of improving the combing property after rinsing when the cleansing composition of the present invention is applied to hair and the viewpoint of imparting good manageability to hair after drying. From the same viewpoints, a preferred embodiment of $R^{13}$ is the same as the preferred embodiment of $R^{10}$ in Formula (5). Furthermore, from the same viewpoints, $R^{14}$ and $R^{15}$ are each preferably a methyl group or an ethyl group.

No particular limitation is imposed on $Z^-$ as long as it is an anionic group. Specific examples thereof include alkyl sulfate ions, sulfate ions, phosphate ions, alkyl carboxylate ions, and halide ions. In particular, from the viewpoints of easiness in production and availability, halide ions are preferred. Examples of the halide ion include fluoride ions, chloride ions, bromide ions, and iodide ions. From the viewpoint of chemical stability, chloride ions and bromide ions are preferred, and chloride ions are more preferred.

Examples of the mineral acid and organic acid salts of the tertiary amines represented by Formula (5) and the quaternary ammonium salt surfactants represented by Formula (6) include mono long-chain alkyl trimethylammonium chlorides, di long-chain alkyl dimethylammonium chlorides, and long-chain tertiary amine salts, and specific examples thereof include mono long-chain alkyl trimethylammonium chlorides such as stearyl trimethylammonium chloride, behenyl trimethylammonium chloride, cetyl trimethylammonium chloride, and stearoxypropyl trimethylammonium chloride; di long-chain alkyl dimethylammonium chlorides such as distearyl dimethylammonium chloride and diisostearyl dimethylammonium chloride; and glutamates, hydrochlorides, citrates, and lactates of mono long-chain diethylamines or mono long-chain dimethylamines such as stearyl dimethylamine, behenyl dimethylamine, octadecyloxypropyl dimethylamine, stearamidoethyl diethylamine, stearamidopropyl dimethylamine, and behenamidopropyl dimethylamine, and the like. From the viewpoints of improving finger combability and manageability after drying of the hair treated with the cleansing composition of the present invention, behenyl trimethylammonium chloride, cetyl trimethylammonium chloride, stearoxypropyl trimethylammonium chloride, stearyl dimethylamine, stearamidopropyl dimethylamine, and behenamidopropyl dimethylamine are preferred.

The content of the component (C) is preferably 50% by mass or less, more preferably 30% by mass or less, more preferably 20% by mass or less, more preferably 15% by mass or less, more preferably 10% by mass or less, and even more preferably 5% by mass or less in the cleansing composition of the present invention, from the viewpoint of imparting good manageability to hair after drying when the hair is treated with the cleansing composition of the present invention and the viewpoint of imparting a moist feeling to skin when the cleansing composition is applied to the body. In addition, the content of the component (C) is preferably 0.5% by mass or more, more preferably 1% by mass or more, and even more preferably 2% by mass or more in the cleansing composition of the present invention, from the viewpoints of improving the appearance and stability of the cleansing composition, improving leathering and foam quality, and improving the feel after rinsing and after drying.

The mass content ratio of the component (A) to the component (C) [component (A)/component (C)] is preferably from 100 to 0.01, more preferably from 20 to 0.1, more preferably from 10 to 0.5, and even more preferably from 5 to 1, from the viewpoint of improving the durability of foam and rinse feel in treatment with the cleansing composition of the present invention, the viewpoint of imparting good manageability to hair after drying when the hair is treated with the cleansing composition of the present invention, and the viewpoint of imparting a moist feeling to skin when the cleansing composition is applied to the body.

<Other Components>

The cleansing composition of the present invention may contain, in addition to the aforementioned components, water, which may serve as a medium in the production of the component (A), a viscosity reducing agent, polyhydric alcohols, a preservative, and a reducing agent, and also, other components used as ordinary cosmetic raw materials. Examples of such a component include a feel improver, a thickener, a fragrance, an ultraviolet absorber, a visible light absorber, a chelating agent, an antioxidant, a colorant, a preservative, a pH adjuster, a viscosity regulator, a pearlescent agent, and a moisturizing agent.

<Production Method of the Cleansing Composition for Skin or Hair>

No particular limitation is imposed on the production method of the cleansing composition of the present invention, and it may be produced by a conventional method. Specifically, for example, in the case of a liquid shampoo for hair, water, the aforementioned component (A), the aforementioned component (B), and if necessary, the aforementioned component (C) are heated and mixed to homogeneity. If necessary, the aforementioned component (A) may be dispersed or dissolved in water in advance, and then added. The cleansing composition of the present invention may also be prepared by adding the aforementioned component (A) to an aqueous solution of a surfactant and homogeneously dissolving or dispersing it, followed by cooling, and if necessary, adding a pearlescent agent, a pH adjuster, a fragrance, a dye, and the like.

No particular limitation is imposed on the form of the cleansing composition of the present invention, and it can be provided in any form such as a liquid, a foam, a paste, a cream, a solid, and a powder, among which a liquid, a paste, or a cream is preferable, and a liquid is more preferable. When the cleansing composition is provided as a liquid, polyethylene glycol, ethanol, and the like are preferably used as a liquid medium in addition to water. The content of water in the cleansing composition of the present invention is preferably 10% by mass or more and 95% by mass or less.

<Intended Use and Method of Use>

The cleansing composition of the present invention can impart not only a durability of foam and good rinse feel, combing property and softness after rinsing, and the manageability after drying to hair, but also a moist feeling to skin; therefore, it can be preferably used as a cleansing composition for hair or a cleansing composition for skin. Examples of the cleansing composition for hair include a hair shampoo. Examples of the cleansing composition for skin include a body shampoo, a facial cleanser, a makeup remover, or a hand soap.

Because the cleansing composition of the present invention can impart not only a good durability of foam and rinse feel, combing property and softness after rinsing, and the manageability after drying to hair, but also a moist feeling to skin, a method for washing the hair which includes applying the aforementioned cleansing composition of the present invention to hair, followed by washing and then rinsing is also provided. Also, a method for washing the body which includes applying the aforementioned cleansing composition of the present invention to a surface of the skin, followed by washing and then rinsing is also provided.

Pertaining to the aforementioned embodiments, the present invention further discloses the following cleansing composition for skin or hair and a method for washing the hair and a method for washing the body using the above cleansing composition for skin or hair.

[1] A cleansing composition for skin or hair, comprising the following (A) and (B):

(A) an internal olefin sulfonate having 12 or more and 24 or less carbon atoms; and (B) an oil solution having a solubility of from 0 to 1 g in 100 g of water at 20° C.

[2] The cleansing composition for skin or hair according to the aforementioned [1], wherein the number of carbon atoms in the internal olefin sulfonate is preferably 14 or more, more preferably 16 or more, and preferably is 20 or less, and more preferably 18 or less.

[3] The cleansing composition for skin or hair according to the aforementioned [1] or [2], wherein the content mass ratio (internal olefin sulfonate having 16 carbon atoms/internal olefin sulfonate having 18 carbon atoms) of an internal olefin sulfonate having 16 carbon atoms to an internal olefin sulfonate having 18 carbon atoms in the component (A) is preferably from 50/50 to 99/1, more preferably from 60/40 to 95/5, more preferably from 70/30 to 90/10, more preferably from 75/25 to 90/10, more preferably from 75/25 to 85/15, and even more preferably from 78/22 to 85/15.

[4] The cleansing composition for skin or hair according to any one of the aforementioned [1] to [3], wherein the total content of an internal olefin sulfonate having 16 carbon atoms and an internal olefin sulfonate having 18 carbon atoms in the component (A) is preferably 50% by mass or more, more preferably 60% by mass, more preferably 70% by mass, more preferably 80% by mass or more, more preferably 90% by mass or more, and even more preferably 95% by mass or more.

[5] The cleansing composition for skin or hair according to any one of the aforementioned [1] to [4], wherein a content of an internal olefin sulfonate in which a sulfonate group is present at the C-2 position in the component (A) is preferably 25% by mass or less, more preferably 24% by mass or less, more preferably 23% by mass or less, more preferably 22% by mass or less, more preferably 20% by mass or less, more preferably less than 20% by mass, more preferably 19% by mass or less, and even more preferably 18% by mass or less.

[6] The cleansing composition for skin or hair according to any one of the aforementioned [1] to [5], wherein a content of an internal olefin sulfonate in which a sulfonate group is present at a C-2 position in the component (A) is preferably 5% by mass or more and 25% by mass or less, more preferably 5% by mass or more and 24% by mass or less, more preferably 5% by mass or more and 23% by mass or less, more preferably 5% by mass or more and 22% by mass or less, preferably 5% by mass or more and 20% by mass or less, more preferably 6% by mass or more and less than 20% by mass, more preferably 7% by mass or more and 19% by mass or less, and even more preferably 8% by mass or more and 18% by mass or less.

[7] The cleansing composition for skin or hair according to any one of the aforementioned [1] to [6], wherein a content of the internal olefin sulfonate in which a sulfonate group is present at the C-2 position in the component (A) is preferably 9% by mass or more and 17.5% by mass or less, more preferably 9% by mass or more and 15% by mass or less, more preferably 9% by mass or more and 12% by mass or less, and even more preferably 9% by mass or more and 10% by mass or less.

[8] The cleansing composition for skin or hair according to any one of the aforementioned [1] to [7], wherein a content of the internal olefin sulfonate in which a sulfonate group is present at the C-2 position in the component (A) is preferably 9% by mass or more and 18% by mass or less, more preferably 10% by mass or more and 18% by mass or less, more preferably 12% by mass or more and 18% by mass or less, more preferably 14% by mass or more and 18% by mass or less, and even more preferably 16% by mass or more and 18% by mass or less.

[9] The cleansing composition for skin or hair according to any one of the aforementioned [1] to [8], wherein a content of an internal olefin sulfonate in which a sulfonate group is present at the C-2 position in the component (A) is preferably 5% by mass or more, more preferably 6% by mass or more, more preferably 7% by mass or more, more preferably 8% by mass or more, more preferably 9% by mass or more, more preferably 10% by mass or more, more preferably 12% by mass or more, more preferably 14% by mass or more, and even more preferably 16% by mass or more.

[10] The cleansing composition for skin or hair according to any one of the aforementioned [1] to [9], wherein a content of an internal olefin sulfonate in which the sulfonate group is present at the C-2 position in the component (A) is preferably 20% by mass or less, more preferably less than 20% by mass, more preferably 19% by mass or less, more preferably less than 18% by mass, even more preferably 17.5% by mass or less, and is preferably 5% by mass or more, more preferably 6% by mass or more, more preferably 7% by mass or more, more preferably 8% by mass or more, and even more preferably 9% by mass or more.

[11] The cleansing composition for skin or hair according to any one of the aforementioned [1] to [10], wherein a content of an internal olefin sulfonate in which the sulfonate group is present at the C-1 position of the olefin chain or alkane chain in the component (A) is preferably 3.0% by mass or less, more preferably 2.5% by mass or less, more preferably 2.0% by mass or less, more preferably 1.5% by mass or less, even more preferably 1.0% by mass or less, and is preferably 0.01% by mass or more.

[12] The cleansing composition for skin or hair according to any one of the aforementioned [1] to [11], wherein the content mass ratio (hydroxy form/olefin form) of the hydroxy form of an internal olefin sulfonate to the olefin form of an internal olefin sulfonate in the component (A) is preferably from 50/50 to 100/0, more preferably from 60/40 to 100/0, more preferably from 70/30 to 100/0, more preferably from 75/25 to 100/0, and even more preferably from 75/25 to 95/5.

[13] The cleansing composition for skin or hair according to any one of the aforementioned [1] to [12], wherein when the component (A) is obtained by a sulfonation of a raw material internal olefin, followed by neutralization and then hydrolysis, the content of an internal olefin in which the double bond is present at the C-2 position in the raw material internal olefin is preferably 40% by mass or less, more preferably 35% by mass or less, more preferably 32% by mass or less, and even more preferably 30% by mass or less, and preferably 5% by mass or more, more preferably 6% by mass or more, more preferably 7% by mass or more, more preferably 8% by mass or more, more preferably 9% by mass or more, more preferably 12% by mass or more, and even more preferably 15% by mass or more.

[14] The cleansing composition for skin or hair according to any one of the aforementioned [1] to [13], wherein when the component (A) is obtained by a sulfonation of the raw material internal olefin, followed by neutralization and then hydrolysis, a content of the internal olefin in which the double bond is present at a C-2 position in the raw material internal olefin is preferably 5% by mass or more and 40% by mass or less, more preferably 5% by mass or more and 35% by mass or less, more preferably 5% by mass or more and 32% by mass or less, more preferably 5% by mass or more and 30% by mass or less, preferably 6% by mass or more and 30% by mass or less, more preferably 7% by mass or more and 30% by mass or less, more preferably 8% by mass or more and 30% by mass or less, more preferably 9% by mass or more and 30% by mass or less, more preferably 12% by mass or more and 30% by mass or less, and even more preferably 15% by mass or more and 27% by mass or less.

[15] The cleansing composition for skin or hair according to any one of the aforementioned [1] to [14], wherein when the component (A) is obtained by a sulfonation of the raw material internal olefin, followed by neutralization and then hydrolysis, a content of the internal olefin in which the double bond is present at a C-2 position in the raw material internal olefin is preferably 15% by mass or more and 25% by mass or less, more preferably 15% by mass or more and 20% by mass or less, more preferably 15% by mass or more and less than 20% by mass, more preferably 15% by mass or more and 19% by mass or less, and even more preferably 15% by mass or more and 18% by mass or less.

[16] The cleansing composition for skin or hair according to any one of the aforementioned [1] to [15], wherein when the component (A) is obtained by a sulfonation of the raw material internal olefin, followed by neutralization and then hydrolysis, a content of the internal olefin in which the double bond is present, at a C-2 position in the raw material internal olefin is preferably 20% by mass or more and 27% by mass or less, more preferably 22% by mass or more and 27% by mass or less, and even more preferably 24% by mass or more and 27% by mass or less.

[17] The cleansing composition for skin or hair according to any one of the aforementioned [1] to [16], wherein the content of the component (A) in the cleansing composition is preferably 0.1% by mass or more, more preferably 1% by mass or more, more preferably 2% by mass or more, even more preferably 5% by mass or more, and is preferably 80% by mass or less, more preferably 50% by mass or less, more preferably 30% by mass or less, and even more preferably 20% by mass or less. [18] The cleansing composition for skin or hair according to any one of the aforementioned [1] to [17], wherein a content of the raw material internal olefin in the component (A) is preferably less than 5.0% by mass, more preferably less than 3.0% by mass, more preferably less than 1.5% by mass, and even more preferably less than 1.0% by mass in the component (A).

[19] The cleansing composition for skin or hair according to any one of the aforementioned [1] to [18], wherein a content of the inorganic compounds in the component (A) is preferably less than 7.5% by mass, more preferably less than 5.0% by mass, more preferably less than 3.0% by mass, more preferably less than 2.0% by mass, and even more preferably less than 1.6% by mass in the component (A).

[20] The cleansing composition for skin or hair according to any one of the aforementioned [1] to [19], wherein an oil solution (B) is preferably one or two or more selected from ester oils, silicone oils, ether oils, hydrocarbon oils, higher alcohols, and carboxylic acids having a hydrocarbon group having from 17 to 23 carbon atoms which may be substituted by a hydroxyl group; preferably one or two or more selected from ester oils, silicone oils, ether oils, hydrocarbon oils, higher alcohols, and carboxylic acids having a hydrocarbon group having 17 to 23 carbon atoms which may be substituted by a hydroxyl group; more preferably one or two or more selected from ester oils, silicone oils, ether oils, hydrocarbon oils, and higher alcohols; and even more preferably one or two or more selected from ester oils, silicone oils, ether oils, and higher alcohols.

[21] The cleansing composition for skin or hair according to any one of the aspects [1] to [20], wherein component (B) has preferably a solubility of from 0 to 0.5 g in 100 g of water at 20° C., and more preferably a solubility of from 0 to 0.1 g in 100 g of water at 20° C.

[22] The cleansing composition for skin or hair according to any one of the aforementioned [1] to [21], wherein the content of the component (B) is preferably 0.01% by mass or more, more preferably 0.03% by mass or more, even more preferably 0.05% by mass or more, and is preferably 30% by mass or less, more preferably 20% by mass or less, and even more preferably 15% by mass or less.

[23] The cleansing composition for skin or hair according to any one of the aspects [1] to [22], wherein the content of oil solution (B) is preferably from 0.1 to 10% by mass and more preferably from 0.5 to 8% by mass when the cleansing composition of the present invention is for hair, and the content of component (B) is preferably from 0.1 to 20% by mass and more preferably from 1 to 10% by mass when the cleansing composition of the present invention is for skin.

[24] The cleansing composition for skin or hair according to any one of the aforementioned [1] to [23], wherein the mass content ratio of the component (A) to the component (B), [Component (A)/Component (B)], is preferably from 0.2 to 1000, more preferably from 0.5 to 200, more preferably from 1 to 100, and even more preferably from 5 to 50.

[25] The cleansing composition for skin or hair according to any one of the aforementioned [1] to [24], further comprising a surfactant (C) other than the component (A).

[26] The cleansing composition for skin or hair according to the aforementioned [25], wherein the component (C) is preferably one or two or more selected from a sulfuric acid ester salt, a sulfonic acid salt, a carboxylic acid salt, a phosphoric acid ester salt, and an amino acid salt.

[27] The cleansing composition for skin or hair according to any one of the aforementioned [25] or [26], wherein the content of the component (C) is preferably 50% by mass or less, more preferably 30% by mass or less, more preferably 20% by mass or less, more preferably 15% by mass or less, more preferably 10% by mass or less, even more preferably 5% by mass or less, and is preferably 0.5% by mass or more, more preferably 1% by mass or more, and even more preferably 2% by mass or more.

[28] The cleansing composition for skin or hair according to any one of the aforementioned [25] to [27], wherein the mass content ratio of the component (A) to the component (C), [Component (A)/Component (C)], is preferably from 100 to 0.01, more preferably from 20 to 0.1, more preferably from 10 to 0.5, and even more preferably from 5 to 1.

[29] A method for washing the hair, comprising applying the cleansing composition for skin or hair according to any one of the aforementioned [1] to [28] to hair, followed by washing and then rinsing.

[30] A method for washing the body, comprising applying the cleansing composition for skin or hair according to any one of the aforementioned [1] to [28] to a surface of the skin, followed by washing and then rinsing.

[31] A method for imparting to hair combing property after rinsing and manageability after drying, comprising applying the cleansing composition for skin or hair according to any one of the aforementioned [1] to [28] to hair.

[32] A method for imparting moist feeling to skin, comprising applying the cleansing composition for skin or hair according to any one of the aforementioned [1] to [28] to skin.

[33] The cleansing composition for skin or hair according to any one of the aforementioned [1] to [28] for washing hair.

[34] The cleansing composition for skin or hair according to any one of the aforementioned [1] to [28] for washing skin.

[35] Use of the cleansing composition for skin or hair according to any one of the aforementioned [1] to [28] for washing hair.

[36] Use of the cleansing composition for skin or hair according to any one of the aforementioned [1] to [28] for washing skin.

[37] The cleansing composition for skin or hair according to any one of the aforementioned [1] to [28] for imparting to hair combing property after rinsing and manageability after drying.

[38] The cleansing composition for skin or hair according to any one of the aforementioned [1] to [28] for imparting moist feeling to skin.

[39] Use of the cleansing composition for skin or hair according to any one of the aforementioned [1] to [28] for imparting to hair combing property after rinsing and manageability after drying.

[40] Use of the cleansing composition for skin or hair according to any one of the aforementioned [1] to [28] for imparting moist feeling to skin.

[41] The cleansing composition for skin or hair according to any one of the aforementioned [1] to [28] for improving foam durability.

[42] The cleansing composition for skin or hair according to any one of the aforementioned [1] to [28] for improving rinse feel.

EXAMPLES

Hereinbelow, the present invention will be specifically described with reference to Examples. It should be noted that unless otherwise specifically noted, “part” means “part by mass” and “%” means “% by mass” in the following Examples and Comparative Examples. Also, the methods used for measuring various physical properties are as follows.

(1) Conditions of Measurement (i) Method for Measuring the Position of a Double Bond in the Raw Material Internal Olefin The position of a double bond in a raw material internal olefin was measured by gas chromatography (hereinbelow, abbreviated as GC). Specifically, an internal olefin was converted to a dithiated derivative by reaction with dimethyl disulfide, and each component was separated by GC. As a result, the position of a double bond in an internal olefin was found based on the peak area of each component.

The apparatus and analytical conditions used for the measurement are as follows. GC apparatus (trade name: HP6890, the product of Hewlett-Packard Company); Column (trade name: Ultra-Alloy-1HT capillary column, 30 m×250 μm×0.15 μm, the product of Frontier Laboratories Ltd.); Detector (flame ionization detector (FID)); Injection temperature of 300° C.; Detector temperature of 350° C.; and He flow rate of 4.6 mL/minute.

(ii) Method for Measuring the Mass Ratio of Hydroxy Form/Olefin Form

The mass ratio of hydroxy form/olefin form of the internal olefin sulfonate was measured by HPLC-MS. Specifically, the hydroxy form and the olefin form were separated by HPLC and each form was identified by separately analyzing with MS. As a result, from the resulting HPLC-MS peak area, the fraction of each form was obtained.

The apparatus and analytical conditions used for the measurement are as follows. HPLC apparatus (trade name: Agilent technology 1100, the product of Agilent Technologies, Inc.); Column (trade name: L-column ODS 4.6×150 mm, the product of Chemicals Evaluation and Research Institute, Japan); Sample preparation (diluted 1000-fold with methanol); Eluent A (10 mM ammonium acetate in water); Eluent B (10 mM ammonium acetate in methanol), Gradient (0 minute (A/B=30/70%)→10 minutes (30/70%)→55 minutes (0/100%)→65 minutes (0/100%)→66 minutes (30/70%)→75 minutes (30/70%)); MS apparatus (trade name: Agilent technology 1100 MS SL (G1946D)); and MS detection (anion detection m/z 60-1600, UV 240 nm).

(iii) Method for Measuring the Content of the Raw Material Internal Olefin

The content of the raw material internal olefin of the internal olefin sulfonate was measured by GC. Specifically, ethanol and petroleum ether were added to an aqueous solution of internal olefin sulfonate, followed by extraction to give olefin in the petroleum ether phase. As a result, from the GC peak area of the olefin, the amount thereof was quantitated. The apparatus and analytical conditions used for the measurement are as follows. GC apparatus (trade name: Agilent technology 6850, the product of Agilent Technologies, Inc.); Column (trade name: Ultra-Alloy-1HT capillary column, 15 m×250 μm×0.15 μm, the product of Frontier Laboratories, Ltd.); Detector (flame ionization detector (FID)); Injection temperature of 300° C.; Detector temperature of 350° C.; and He flow rate of 3.8 mL/minute.

(iv) Method for Measuring the Content of Inorganic Compounds

The content of inorganic compounds was measured by potentiometric titration and neutralization titration. Specifically, the content of $Na_2SO_4$ was quantitated by measuring sulfate ion ($SO_4^{2-}$) by potentiometric titration. Also, the content of NaOH was quantitated by neutralization titration with diluted hydrochloric acid.

(v) Method for Measuring the Content of the Paraffin Component

The content of the paraffin component was measured by GC. Specifically, ethanol and petroleum ether were added to an aqueous solution of internal olefin sulfonate, followed by extraction to give paraffin in the petroleum ether phase. As a result, from the GC peak area of the paraffin, the amount thereof was quantitated. It should be noted that the apparatus and analytical conditions used for measurement are the same as those used for the measurement of the content of the raw material internal olefin.

(vi) Method for Measuring the Content of Internal Olefin Sulfonate in which a Sulfonate Group is Present at a C-2 Position The linkage position of the sulfonate group was measured by GC. Specifically, the resulting internal olefin sulfonate (A) was reacted with trimethylsilyldiazomethane to form a methyl-esterified derivative. Then, each component was separated by GC. Each of a peak area was regarded as a mass ratio, and the content of internal olefin sulfonate in which a sulfonate group is present at a C-2 position was quantitated.

The apparatus and analytical conditions used for the measurement are as follows. GC apparatus (trade name: Agilent technology 6850, the product of Agilent Technologies, Inc.); Column (trade name: HP-1 capillary column, 30 m×320 μm×0.25 μm, the product of Agilent Technologies, Inc.); Detector (hydrogen flame ionization detector (FID)); Injection temperature of 300° C.; Detector temperature of 300° C.; He flow rate of 1.0 mL/min.; oven (60° C. (0 min.)→10° C./min.→300° C. (10 min.)).

(2) Production of an Internal Olefin

Production Example A

Into a flask with a stirrer, 7000 g (25.9 moles) of 1-octadecanol (trade name: KALCOL 8098, the product of Kao Corporation), and as a solid acid catalyst, 1050 g (15 wt % relative to the raw material alcohol) of γ-alumina (STREM Chemicals, Inc.) were placed, and reactions were allowed to proceed for 13 hours at 285° C. while stirring and passing nitrogen (7000 mL/minute) through the system. The alcohol conversion ratio was 100% and the purity of C18 internal olefin was 98.5% after the completion of the reaction. The resulting crude internal olefin was transferred to a distillation flask and distilled at from 148 to 158° C./0.5 mmHg, whereby 100% pure internal olefin having 18 carbon atoms was obtained. The double bond distribution in the resulting internal olefin was 0.7% by mass at C-1 position, 16.9% by mass at C-2 position, 15.9% by mass at C-3 position, 16.0% by mass at C-4 position, 14.7% by mass at C-5 position, 11.2% by mass at C-6 position, 10.2% by mass at C-7 position, and 14.6% by mass in total at C-8 and 9 positions.

Production Example B

Into a flask with a stirrer, 7000 g (28.9 moles) of 1-hexadecanol (trade name: KALCOL 6098, the product of Kao Corporation), and as a solid acid catalyst, 700 g (10% by mass relative to the raw material alcohol) of γ-alumina (STREM Chemicals, Inc.) were placed, and reactions were allowed to proceed for five hours at 280° C. while stirring and passing nitrogen (7000 mL/minute) through the system. The alcohol conversion ratio was 100%, and the purity of C16 internal olefin was 99.7% after the completion of the reaction. The resulting crude internal olefin was transferred to a distillation flask and distilled at from 136 to 160° C./4.0 mmHg, whereby 100% pure internal olefin having 16 carbon atoms was obtained. The double bond distribution in the resulting internal olefin was 0.5% by mass at C-1 position, 16.5% by mass at C-2 position, 15.4% by mass at C-3 position, 16.4% by mass at C-4 position, 17.2% by mass at C-5 position, 14.2% by mass at C-6 position, and 19.8% by mass in total at C-7 and 8 positions.

Production Example C

Into a flask with a stirrer, 7000 g (28.9 moles) of 1-hexadecanol (trade name: KALCOL 6098, the product of Kao Corporation), and as a solid acid catalyst, 700 g (10 wt % relative to the raw material alcohol) of γ-alumina (STREM Chemicals, Inc.) were placed, and reactions were allowed to proceed for three hours at 280° C. while stirring and passing nitrogen (7000 mL/minute) through the system. The alcohol conversion ratio was 100%, and the purity of C16 internal olefin was 99.6% after the completion of the reaction. The resulting crude internal olefin was transferred to a distillation flask and distilled at from 136 to 160° C./4.0 mmHg, whereby 100% pure internal olefin having 16 carbon atoms was obtained. The double bond distribution in the resulting internal olefin was 1.8% by mass at C-1 position, 30.4% by mass at C-2 position, 23.9% by mass at C-3 position, 16.8% by mass at C-4 position, 12.0% by mass at C-5 position, 7.4% by mass at C-6 position, and 7.8% by mass in total at C-7 and 8 positions.

Production Example D

Into a flask with a stirrer, 7000 g (25.9 moles) of 1-octadecanol (trade name: KALCOL 8098, the product of Kao Corporation), and as a solid acid catalyst, 700 g (10 wt % relative to the raw material alcohol) of γ-alumina (STREM Chemicals, Inc.) were placed, and reactions were allowed to proceed for 10 hours at 280° C. while stirring and passing nitrogen (7000 mL/minute) through the system. The alcohol conversion ratio was 100%, and the purity of C18 internal olefin was 98.2% after the completion of the reaction. The resulting crude internal olefin was transferred to a distillation flask and distilled at the temperature inside of from 148 to 158° C./0.5 mmHg, whereby 100% pure purified internal olefin having 18 carbon atoms was obtained. The double bond distribution in the resulting internal olefin was 0.8% by mass at C-1 position; 31.3% by mass at C-2 position; 22.9% by mass at C-3 position; 15.5% by mass at C-4 position; 10.8% by mass at C-5 position; 7.2% by mass at C-6 position; 5.3% by mass at C-7 position; and 6.2% by mass in total at C-8 and 9 positions.

Production Example E

A reaction time was adjusted in a same manner as Production Example C, in order to produce C16 internal olefin having 100% of purity. The double bond distribution of the resulting internal olefin was 0.8% by mass at a C-1 position, 26.8% by mass at a C-2 position, 22.6% by mass at a C-3 position, 18.2% by mass at a C-4 position, 16.5% by mass at a C-5 position, 8.5% by mass at a C-6 position, and 6.6% by mass in total at C-7 and C-8 positions.

Production Example F

A reaction time was adjusted in a same manner as Production Example D, in order to produce C18 internal olefin having 100% of purity. The double bond distribution of the resulting internal olefin was 0.3% by mass at a C-1 position, 19.0% by mass at a C-2 position, 17.6% by mass at a C-3 position, 17.4% by mass at a C-4 position, 14.9% by mass at a C-5 position, 12.3% by mass at a C-6 position, 8.8% by mass at a C-7 position, and 9.8% by mass in total at C-8 and C-9 positions.

Production Example G 11.9 kg of the C16 internal olefin obtained in the Production Example E and 3.1 kg of the C18 internal olefin obtained in Production Example F were mixed to produce 15.0 kg of C16/C18 (mass ratio of 79.4/20.6) internal olefin. The double bond distribution of the resulting internal olefin was 0.7% by mass at a C-1 position, 25.2% by mass at a C-2 position, 21.6% by mass at a C-3 position, 18.0% by mass at a C-4 position, 16.2% by mass at a C-5 position, 9.3% by mass at a C-6 position, 4.4% by mass at a C-7 position, 3.6% by mass at a C-8 position, and 1.0% by mass at a C-9 position.

Production Example H

A reaction time was adjusted in a same manner as Production Example C, in order to produce C16 internal olefin having 100% of purity. The double bond distribution of the resulting internal olefin was 0.5% by mass at a C-1 position, 30.1% by mass at a C-2 position, 25.5% by mass at a C-3 position, 18.9% by mass at a C-4 position, 11.1% by mass at a C-5 position, 7.0% by mass at a C-6 position, and 7.0% by mass in total at C-7 and C-8 positions.

Production Example I

A reaction time was adjusted in a same manner as Production Example D, in order to produce C18 internal olefin having 100% of purity. The double bond distribution of the resulting internal olefin was 0.5% by mass at a C-1 position, 25.0% by mass at a C-2 position, 22.8% by mass at a C-3 position, 19.1% by mass at a C-4 position, 14.0% by mass at a C-5 position, 7.4% by mass at a C-6 position, 5.4% by mass at a C-7 position, and 5.8% by mass in total at C-8 and C-9 positions.

Production Example J

Into a flask with a stirrer, 6000 g (30.6 moles) of 1-tetradecene (trade name: LINEALENE 14, the product of Idemitsu Kosan Co., Ltd.), and as a solid acid catalyst, 173 g (2.9 wt % relative to the raw material 1-tetradecene) of β-zeolite (Zeolyst International, Inc.) were placed, and reactions were allowed to proceed for 21 hours at 120° C. while stirring and passing nitrogen (200 mL/minute) through the system. The internal isomerization ratio of α-olefin was 99.0%, and the purity of C14 internal olefin was 91.1% after the completion of the reaction. The resulting crude internal olefin was transferred to a distillation flask and distilled at from 130 to 136° C./from 12.8 to 13.5 mmHg, whereby 100% pure internal olefin having 14 carbon atoms was obtained. The double bond distribution of the resulting internal olefin was 1.3% by mass at C-1 position, 31.8% by mass at C-2 position, 23.8% by mass at C-3 position, 21.0% by mass at C-4 position, 8.6% by mass at C-5 position, and 13.6% by mass in total at C-6 and C-7 positions.

Production Example K

Into a flask with a stirrer, 6000 g (35.6 moles) of 1-dodecene (trade name: LINEALENE 12, the product of Idemitsu Kosan Co., Ltd.), and as a solid acid catalyst, 180 g (3.0 wt % relative to the raw material 1-dodecene) of β-zeolite (Zeolyst International, Inc.) were placed, and reactions were allowed to proceed for 12.5 hours at 120° C. while stirring and passing nitrogen (200 mL/minute) through the system. The internal isomerization ratio of α-olefin was 98.4%, and the purity of C12 internal olefin was 92.1% after the completion of the reaction. The resulting crude internal olefin was transferred to a distillation flask and distilled at from 134 to 138° C./from 75.0 to 78.8 mmHg, whereby 100% pure internal olefin having 12 carbon atoms was obtained. The double bond distribution of the resulting internal olefin was 0.5% by mass at C-1 position, 33.1% by mass at C-2 position, 23.7% by mass at C-3 position, 21.2% by mass at C-4 position, 15.0% by mass at C-5 position, and 6.8% by mass at C-6 position.

(3) Production of an Internal Olefin Sulfonate

Production Example 1

Using a thin film sulfonation reactor (14 mm in inner diameter and 4 m in length), the sulfonation reaction of the internal olefin having 16 carbon atoms produced in Production Example C was carried out by passing through sulfur trioxide gas containing a concentration of $SO_3$ at 2.8% by volume, while passing cooling water of 20° C. through the outer jacket of the reactor. It should be noted that the reaction molar ratio of $SO_3$/internal olefin was set at 1.09.

The resulting sulfonate was added to an alkaline aqueous solution containing 1.2 times the molar amount of sodium hydroxide relative to the theoretical acid value (AV), followed by neutralization at 30° C. for one hour while stirring. The resulting neutralized product was hydrolyzed by heating at 160° C. for one hour in an autoclave, whereby a crude product of sodium C16 internal olefin sulfonate was obtained.

Then, 300 g of the crude product thus obtained was transferred to a separatory funnel, to which 300 mL of ethanol was added. Then, 300 mL of petroleum ether was added per operation, whereby oil-soluble impurities were removed by extraction. At this time, inorganic compounds (mainly composed of sodium sulfate) which were precipitated at the oil-water interface by the addition of ethanol were also separated and removed from the aqueous phase by the oil-water separation operation. The above operation was repeated three times. Then, the aqueous phase side was evaporated to dryness, whereby sodium internal olefin sulfonate (1) having 16 carbon atoms was obtained. The content of the raw material internal olefin was less than 100 ppm (below the GC detection limit) and that of inorganic compounds was 1.9% by mass. The above results are shown in Table 1.

Production Example 2

Except for using the internal olefin having 18 carbon atoms produced in Production Example D, sodium internal olefin sulfonate (2) having 18 carbon atoms was obtained under the same conditions as those used in Production Example 1. The content of the raw material internal olefin was less than 100 ppm (below the GC detection limit) and that of inorganic compounds was 0.9% by mass. The above results are shown in Table 1.

Production Example 3

Except for using the internal olefin having 16 carbon atoms produced in Production Example B, sodium internal olefin sulfonate (3) having 16 carbon atoms was obtained under the same conditions as those used in Production Example 1. The content of the raw material internal olefin was less than 100 ppm (below the GC detection limit) and that of inorganic compounds was 1.3% by mass. The above results are shown in Table 1.

Production Example 4

Except for using the internal olefin having 18 carbon atoms produced in Production Example A, sodium internal olefin sulfonate having (4) 18 carbon atoms was obtained under the same conditions as those used in Production Example 1. The content of the raw material internal olefin was less than 100 ppm (below the GC detection limit) and that of inorganic compounds was 1.7% by mass. The above results are shown in Table 1.

Production Example 5

The C16/18 internal olefin (the content of internal olefin in which double bonds are present at C-2 position is 25.2% by mass) produced in Production Example G was used as a raw material, and a sodium C16/C18 internal olefin sulfonate (5) was obtained by the same manner as in Production Example 1. The mass ratio of hydroxy form (sodium hydroxyalkane sulfonate)/olefin form (sodium olefin sulfonate) in the obtained sodium internal olefin sulfonate was 87/13. Also, the content of the raw material internal olefin contained in the obtained sodium internal olefin sulfonate was less than 100 ppm (below the GC detection limit) and that of inorganic compounds was 0.5% by mass.

Production Example 6

Except for using the internal olefin having 16 carbon atoms produced in Production Example H, sodium internal olefin sulfonate (6) having 16 carbon atoms was obtained under the same conditions as those used in Production Example 1. The content of the raw material internal olefin was less than 100 ppm (below the GC detection limit) and that of inorganic compounds was 0.2% by mass. The above results are shown in Table 1.

Production Example 7

Except for using the internal olefin having 18 carbon atoms produced in Production Example I, sodium internal olefin sulfonate (7) having 18 carbon atoms was obtained under the same conditions as those used in Production Example 1. The content of the raw material internal olefin was less than 100 ppm (below the GC detection limit) and that of inorganic compounds was 0.1% by mass. The above results are shown in Table 1.

Production Example 8

Except for using the internal olefin having 14 carbon atoms produced in Production Example J, sodium internal olefin sulfonate (8) having 14 carbon atoms was obtained under the same conditions as those used in Production Example 1. The content of the raw material internal olefin was less than 100 ppm (below the GC detection limit) and that of inorganic compounds was 0.5% by mass. The above results are shown in Table 1.

Production Example 9

Except for using the internal olefin having 12 carbon atoms produced in Production Example K, sodium internal olefin sulfonate (9) having 12 carbon atoms was obtained under the same conditions as those used in Production Example 1. The content of the raw material internal olefin was less than 100 ppm (below the GC detection limit) and that of inorganic compounds was 0.2% by mass. The above results are shown in Table 1.

TABLE 1

| | Raw material internal olefin | | Internal olefin sulfonate | |
|---|---|---|---|---|
| | Number of carbon atoms | C-2 Double bond (%) | HAS/IOS (Mass ratio) | Content of internal olefin sulfonate in which sulfonate group is present at C-2 position (%) |
| Internal olefin sulfonate (1) | C16 | 30.4 | 80/20 | 20.3 |
| Internal olefin sulfonate (2) | C18 | 31.3 | 80/20 | 21.4 |
| Internal olefin sulfonate (3) | C16 | 16.5 | 80/20 | 9.3 |
| Internal olefin sulfonate (4) | C18 | 16.9 | 80/20 | 9.6 |
| Internal olefin sulfonate (5) | C16/C18 | 25.2 | 87/13 | 17.6 |
| Internal olefin sulfonate (6) | C16 | 30.1 | 80/20 | 19.9 |
| Internal olefin sulfonate (7) | C18 | 25.0 | 80/20 | 15.0 |
| Internal olefin sulfonate (8) | C14 | 31.8 | 92.8/7.4 | 22.0 |
| Internal olefin sulfonate (9) | C12 | 33.1 | 80/20 | 21.0 |

(4) Preparation of the Cleansing Compositions

Using internal olefin sulfonates shown in Table 1, the cleansing compositions for hair or skin each having the compositions shown in Tables 2 to 4 were prepared by a conventional method. Specifically, the component (A), the component (B), and appropriate amounts of water, and if necessary, the component (C) were placed in a beaker. The resulting mixture was heated to 60° C. and mixed, and then cooled to room temperature. Then, the mixture was supplemented with water and adjusted to pH 6 with a pH adjuster (a 50% aqueous solution of citric acid or a 10% aqueous solution of sodium hydroxide), whereby each cleansing composition was obtained.

(5) Hair Evaluation after Washing

Each of the following components was placed in a beaker and heated to 80° C., followed by mixing. After confirming homogeneous dissolution, the mixture was cooled to give a plain shampoo. A hair bundle (Japanese hair which was not subjected to treatment such as bleaching and hair coloring, approximately 20 cm long, 15 g) was washed with the plain shampoo thus obtained, whereby a tress for evaluation was obtained.

(Composition of the Plain Shampoo)

| (Component) | (% by mass) |
|---|---|
| Sodium polyoxyethylene lauryl ether sulfate (42.0% as EMAL E-27C (the product of Kao Corporation, active content, 27% by mass)) | 11.3 |
| Coconut oil fatty acid N-methyl ethanolamide (AMINON C-11S (the product of Kao Corporation)) | 3.0 |
| Citric acid | 0.2 |
| Methylparaben | 0.3 |
| Purified water | Balance |
| Total | 100.0 |

The tress for evaluation thus obtained was washed with each cleansing composition, and was evaluated for the rinse feel after washing, combing property of the hair after rinsing, and manageability of the hair after drying by five expert panelists based on the following evaluation criteria and evaluation method.

Also, in order to evaluate a foam retention (durability) in the presence of an oily component such as stain of sebum, 0.05 ml of model sebum was applied to the hair, and was washed. Then, foam durability during washing was evaluated. The model sebum was prepared by uniformly mixing 4/1% by mass of triolein/lanolin at 40° C.

The results are shown in Tables 2 and 3.

(Evaluation Criteria and Evaluation Method)

Rinse Feel

5: Excellent rinse feel
4: Good rinse feel
3: Fair rinse feel (equivalent to that of Comparative Example 1)
2: Poor rinse feel
1: Very poor rinse feel Combing Property 5: Excellent combing property
4: Good combing property
3: Fair combing property (equivalent to that of Comparative Example 2)
2: Poor combing property
1: Very poor combing property Manageability 5: Excellent hair manageability
4: Good hair manageability
3: Fair hair manageability (equivalent to that of Comparative Example 2)
2: Poor hair manageability
1: Very poor hair manageability Foam Durability 5: Foam durability is very good (not feeling a decrease in the volume of foam during washing)

4: Foam durability is good (less decrease in the volume of foam)

3: Fair foam durability (equivalent to Comparative Example 2)

2: Foam durability was poor (remarkable decrease in the volume of foam)

1: Foam was not maintained (defoaming was found during washing)

TABLE 2

| Cleansing composition for hair (shampoo) | | Examples 1 | 2 | 3 | 4 | 5 | 6 | 7 | 8 | 9 | 10 | 11 | 12 |
|---|---|---|---|---|---|---|---|---|---|---|---|---|---|
| Formulation (% by mass) | (A) Internal olefin sulfonate(1) | 12.0 | | | | | | | | | | | |
| | Internal olefin sulfonate(2) | | 12.0 | | | | | | | | | | |
| | Internal olefin sulfonate(3) | | | 12.0 | | 11.0 | 9.6 | 9.0 | 7.8 | 6.0 | 16.0 | 4.0 | 9.6 |
| | Internal olefin sulfonate(4) | | | | 12.0 | 1.0 | 2.4 | 3.0 | 4.2 | 6.0 | 4.0 | 1.0 | 2.4 |
| | Internal olefin sulfonate(5) | | | | | | | | | | | | |
| | Internal olefin sulfonate(6) | | | | | | | | | | | | |
| | Internal olefin sulfonate(7) | | | | | | | | | | | | |
| | Internal olefin sulfonate(8) | | | | | | | | | | | | |
| | Internal olefin sulfonate(9) | | | | | | | | | | | | |
| | Sodium lauryl ether sulfate *1 | | | | | | | | | | | | |
| | Sodium lauryl sulfate *2 | | | | | | | | | | | | |
| | Sodium α-olefin sulfonate *3 | | | | | | | | | | | | |
| | Secondary alkane sulfonate *4 | | | | | | | | | | | | |
| | Sodium lauryl ether acetate *5 | | | | | | | | | | | | |
| | (B) Silicone *6 | 1.0 | 1.0 | 1.0 | 1.0 | 1.0 | 1.0 | 1.0 | 1.0 | 1.0 | 1.0 | 1.0 | 0.2 |
| | pH Adjuster | | | | | | q.s. | | | | | | |
| | Purified water | | | | | | Balance | | | | | | |
| Content of internal olefin in which double bond is present at C-2 position in raw material internal olefin (% by mass) | | 30.4 | 31.3 | 16.5 | 16.9 | 16.5 | 16.6 | 16.6 | 16.6 | 16.7 | 16.6 | 16.6 | 16.6 |
| C16/C18 Content in component (A) (% by mass) | | 100 | 100 | 100 | 100 | 100 | 100 | 100 | 100 | 100 | 100 | 100 | 100 |
| Content of internal olefin sulfonate in which sulfonate group is present at C-2 position (% by mass) | | 20.3 | 21.4 | 9.3 | 9.6 | 9.3 | 9.4 | 9.4 | 9.4 | 9.5 | 9.4 | 9.4 | 9.4 |
| Evaluation results | Rinse feel | 4.0 | 3.6 | 4.8 | 4.4 | 5.0 | 5.0 | 5.0 | 4.8 | 4.4 | 4.6 | 4.8 | 4.8 |
| | Combing property after rinsing | 4.0 | 4.0 | 4.2 | 4.2 | 4.4 | 4.6 | 4.4 | 4.4 | 4.2 | 4.0 | 4.4 | 4.4 |
| | Manageability after drying | 4.0 | 4.2 | 4.2 | 4.4 | 4.4 | 4.6 | 4.6 | 4.6 | 4.6 | 4.0 | 4.4 | 3.6 |
| | Durability of foam | — | — | — | — | — | 3.6 | — | — | — | — | — | — |

| Cleansing composition for hair (shampoo) | | Examples 13 | 14 | 15 | 16 | 17 | 18 | 19 | 20 | 21 | 22 | 23 | 24 |
|---|---|---|---|---|---|---|---|---|---|---|---|---|---|
| Formulation (% by mass) | (A) Internal olefin sulfonate(1) | | | | | | | | | | | | |
| | Internal olefin sulfonate(2) | | | | | | | | | | | | |
| | Internal olefin sulfonate(3) | 9.6 | | | | | | | | | | | |
| | Internal olefin sulfonate(4) | 2.4 | | | | | | | | | | | |
| | Internal olefin sulfonate(5) | | 12.0 | | | | | | | | | | |
| | Internal olefin sulfonate(6) | | | 12.0 | | 11.0 | 9.6 | 9.0 | 7.8 | 6.0 | 16.0 | 4.0 | 9.6 |
| | Internal olefin sulfonate(7) | | | | 12.0 | 1.0 | 2.4 | 3.0 | 4.2 | 6.0 | 4.0 | 1.0 | 2.4 |
| | Internal olefin sulfonate(8) | | | | | | | | | | | | |
| | Internal olefin sulfonate(9) | | | | | | | | | | | | |
| | Sodium lauryl ether sulfate *1 | | | | | | | | | | | | |
| | Sodium lauryl sulfate *2 | | | | | | | | | | | | |
| | Sodium α-olefin sulfonate *3 | | | | | | | | | | | | |
| | Secondary alkane sulfonate *4 | | | | | | | | | | | | |
| | Sodium lauryl ether acetate *5 | | | | | | | | | | | | |
| | (B) Silicone *6 | 3.0 | 1.0 | 1.0 | 1.0 | 1.0 | 1.0 | 1.0 | 1.0 | 1.0 | 1.0 | 1.0 | 0.2 |
| | pH Adjuster | | | | | | q.s. | | | | | | |
| | Purified water | | | | | | Balance | | | | | | |
| Content of internal olefin in which double bond is present at C-2 position in raw material internal olefin (% by mass) | | 16.6 | 25.2 | 30.1 | 25.0 | 29.7 | 29.1 | 28.8 | 28.3 | 27.6 | 29.1 | 29.1 | 29.1 |
| C16/C18 Content in component (A) (% by mass) | | 100 | 100 | 100 | 100 | 100 | 100 | 100 | 100 | 100 | 100 | 100 | 100 |
| Content of internal olefin sulfonate in which sulfonate group is present at C-2 position (% by mass) | | 9.4 | 17.6 | 19.9 | 15 | 19.5 | 18.9 | 18.7 | 18.2 | 17.5 | 18.9 | 18.9 | 18.9 |
| Evaluation results | Rinse feel | 4.2 | 5.0 | 4.4 | 3.8 | 4.4 | 4.6 | 4.6 | 4.4 | 4.2 | 4.2 | 4.4 | 4.6 |
| | Combing property after rinsing | 4.0 | 4.2 | 3.8 | 4.0 | 4.2 | 4.2 | 4.0 | 4.0 | 4.0 | 4.0 | 4.0 | 4.2 |
| | Manageability after drying | 4.4 | 5.0 | 4.2 | 5.0 | 4.6 | 5.0 | 5.0 | 5.0 | 5.0 | 4.2 | 4.8 | 3.8 |
| | Durability of foam | — | 4.6 | 4.0 | 4.0 | 4.4 | 4.6 | 4.6 | 4.4 | 4.2 | 4.8 | 4.0 | 4.4 |

TABLE 2-continued

| Cleansing composition for hair (shampoo) | | | Examples 25 | 26 | 27 | 28 | 29 | Comparative Examples 1 | 2 | 3 | 4 | 5 | 6 | 7 |
|---|---|---|---|---|---|---|---|---|---|---|---|---|---|---|
| Formulation (% by mass) | (A) | Internal olefin sulfonate(1) | | | | | | | | | | | | |
| | | Internal olefin sulfonate(2) | | | | | | | | 12.0 | | | | |
| | | Internal olefin sulfonate(3) | | | | | | | | | | | | |
| | | Internal olefin sulfonate(4) | | | | | | | | | | | | |
| | | Internal olefin sulfonate(5) | | | | | | | | | | | | |
| | | Internal olefin sulfonate(6) | 9.6 | 4.8 | 2.9 | | | | | | | | | |
| | | Internal olefin sulfonate(7) | 2.4 | 1.2 | 0.7 | | | | | | | | | |
| | | Internal olefin sulfonate(8) | | 6.0 | 8.4 | 12.0 | | | | | | | | |
| | | Internal olefin sulfonate(9) | | | | | 12.0 | | | | | | | |
| | | Sodium lauryl ether sulfate *1 | | | | | | 12.0 | 12.0 | | | | | |
| | | Sodium lauryl sulfate *2 | | | | | | | | | 12.0 | | | |
| | | Sodium α-olefin sulfonate *3 | | | | | | | | | | 12.0 | | |
| | | Secondary alkane sulfonate *4 | | | | | | | | | | | 12.0 | |
| | | Sodium lauryl ether acetate *5 | | | | | | | | | | | | 12.0 |
| | (B) | Silicone *6 | 3.0 | 1.0 | 1.0 | 1.0 | 1.0 | | 1.0 | | 1.0 | 1.0 | 1.0 | 1.0 |
| | | pH Adjuster | | | | | | q.s. | | | | | | |
| | | Purified water | | | | | | Balance | | | | | | |
| | Content of internal olefin in which double bond is present at C-2 position in raw material internal olefin (% by mass) | | 29.1 | 30.4 | 31.0 | 31.8 | 33.1 | | | | | | | |
| | C16/C18 Content in component (A) (% by mass) | | 100 | 50 | 30 | 0 | 0 | | | | | | | |
| | Content of internal olefin sulfonate in which sulfonate group is present at C-2 position (% by mass) | | 18.9 | 20.5 | 21.1 | 22 | 21 | | | | | | | |
| Evaluation results | | Rinse feel | 4.2 | 5.0 | 5.0 | 5.0 | 5.0 | 3.0 | 2.0 | 3.4 | 3.0 | 3.6 | 2.8 | 2.4 |
| | | Combing property after rinsing | 4.0 | 4.0 | 3.8 | 3.8 | 3.4 | 3.2 | 3.0 | 2.4 | 2.0 | 1.8 | 3.0 | 3.6 |
| | | Manageability after drying | 5.0 | 4.8 | 4.8 | 4.6 | 4.6 | 1.8 | 3.0 | 2.4 | 3.2 | 3.0 | 3.0 | 2.0 |
| | | Durability of foam | 4.0 | 4.0 | 3.8 | 3.8 | 3.6 | — | 3.0 | — | — | — | — | — |

*1 Trade name: EMAL 270S (active ingredient 70%) manufactured by Kao Corporation blended in an amount of 17.14%
*2 The product of Kao Corporation, trade name: EMAL 30N-S
*3 The product of Lion Corporation, trade name: LIPOLAN LB-440 (active ingredient 36%) was added at 33.33%.
*4 The product of LANXESS K.K., trade name: Mersolat (active ingredient 95%) was added at 12.63%.
*5 The product of Kao Corporation, trade name: KAO AKVPO RLM-45NV (active ingredient 23.5%) was added at 51.06%.
*6 The product of Dow Corning Toray Co., Ltd., trade name: BY22-050A (active ingredient 55%)

TABLE 3

| Cleansing composition for hair (shampoo) | | | Examples 30 | 31 | 32 | 33 | 34 | 35 | 36 | 37 | 38 | 39 |
|---|---|---|---|---|---|---|---|---|---|---|---|---|
| Formulation (% by mass) | (A) | Internal olefin sulfonate(3) | 9.6 | 9.6 | 9.6 | 9.6 | 9.6 | 9.6 | 9.6 | 9.6 | 9.6 | 9.6 |
| | | Internal olefin sulfonate(4) | 2.4 | 2.4 | 2.4 | 2.4 | 2.4 | 2.4 | 2.4 | 2.4 | 2.4 | 2.4 |
| | | Internal olefin sulfonate(6) | | | | | | | | | | |
| | | Internal olefin sulfonate(7) | | | | | | | | | | |
| | (B) | Myristyl alcohol | 1.0 | | | | | | | | | |
| | | Stearyl alcohol | | 1.0 | | | | | | | | |
| | | Isopropyl palmitate *1 | | | 1.0 | | | | | | | |
| | | Octyl dodecyl myristate *2 | | | | 1.0 | | | | | | |
| | | Dioctyl ether *3 | | | | | 1.0 | | | | | |
| | | Glyceryl isostearate *4 | | | | | | 1.0 | | | | |
| | | Dimethicone *5 | | | | | | | 1.0 | | | |
| | | Dimethiconol *6 | | | | | | | | 1.0 | | |
| | | Amino-modified silicone *7 | | | | | | | | | 1.0 | |
| | | Dimethicone *8 | | | | | | | | | | 1.0 |
| | | pH Adjuster | | | | | q.s. | | | | | |
| | | Purified water | | | | | Balance | | | | | |
| Evaluation results | | Rinse feel | 4.8 | 4.6 | 4.2 | 4.4 | 3.8 | 4.6 | 4.2 | 4.2 | 4.0 | 4.2 |
| | | Combing property after rinsing | 4.2 | 4.4 | 4.0 | 3.8 | 4.2 | 4.2 | 4.0 | 4.0 | 4.4 | 4.0 |
| | | Manageability after drying | 3.6 | 4.0 | 4.0 | 4.2 | 4.8 | 4.0 | 4.2 | 4.4 | 4.8 | 5.0 |
| | | Durability of foam | — | — | — | — | — | — | — | — | — | — |

| Cleansing composition for hair (shampoo) | | | Examples 40 | 41 | 42 | 43 | 44 | 45 | 46 | 47 | 48 | 49 |
|---|---|---|---|---|---|---|---|---|---|---|---|---|
| Formulation (% by mass) | (A) | Internal olefin sulfonate(3) | | | | | | | | | | |
| | | Internal olefin sulfonate(4) | | | | | | | | | | |
| | | Internal olefin sulfonate(6) | 9.6 | 9.6 | 9.6 | 9.6 | 9.6 | 9.6 | 9.6 | 9.6 | 9.6 | 9.6 |
| | | Internal olefin sulfonate(7) | 2.4 | 2.4 | 2.4 | 2.4 | 2.4 | 2.4 | 2.4 | 2.4 | 2.4 | 2.4 |
| | (B) | Myristyl alcohol | 1.0 | | | | | | | | | |

TABLE 3-continued

| | | | | | | | | | | | |
|---|---|---|---|---|---|---|---|---|---|---|---|
| | Stearyl alcohol | | 1.0 | | | | | | | | |
| | Isopropyl palmitate *1 | | | 1.0 | | | | | | | |
| | Octyl dodecyl myristate *2 | | | | 1.0 | | | | | | |
| | Dioctyl ether *3 | | | | | 1.0 | | | | | |
| | Glyceryl isostearate *4 | | | | | | 1.0 | | | | |
| | Dimethicone *5 | | | | | | | 1.0 | | | |
| | Dimethiconol *6 | | | | | | | | 1.0 | | |
| | Amino-modified silicone *7 | | | | | | | | | 1.0 | |
| | Dimethicone *8 | | | | | | | | | | 1.0 |
| | pH Adjuster | q.s. | | | | | | | | | |
| | Purified water | Balance | | | | | | | | | |
| Evaluation results | Rinse feel | 4.6 | 4.2 | 3.8 | 4.2 | 3.6 | 4.4 | 4.0 | 4.0 | 3.8 | 4.2 |
| | Combing property after rinsing | 4.0 | 4.4 | 3.8 | 3.6 | 3.8 | 4.0 | 3.8 | 4.0 | 4.2 | 4.0 |
| | Manageability after drying | 4.0 | 4.6 | 4.4 | 4.4 | 5.0 | 4.2 | 4.4 | 4.8 | 4.8 | 5.0 |
| | Durability of foam | 4.8 | 5.0 | 4.4 | 4.4 | 4.2 | 4.4 | 4.6 | 4.6 | 4.6 | 4.6 |

*1 Trade name: EXCEPARL IPP, manufactured by Kao Corporation
*2 Trade name: EXCEPARL OD-M, manufactured by Kao Corporation
*3 Trade name: Cetiol OE, manufactured by Cognis Ltd.
*4 Trade name: PENETOL GE-IS manufactured by Kao Corporation
*5 Trade name: BY22-029 (active ingredient: 50%) manufactured by Dow Corning Toray Co., Ltd.
*6 Trade name: DC1785 (active ingredient: 50%) manufactured by Dow Corning Toray Co., Ltd.
*7 Trade name: BY22-079 (active ingredient: 14%) manufactured by Dow Corning Toray Co., Ltd.
*8 Trade name: HMN2220 Nonion Emulsion (active ingredient: 60%) manufactured by Dow Corning Toray Co., Ltd.

(6) Skin Evaluation after Washing

Five expert panelists washed their hands with each cleansing composition, and evaluated the rinse feel after washing, and the moist feeling to the skin after towel drying after rinsing, and durability of foam based on the following evaluation criteria and evaluation method. It should be noted that rinse feel was evaluated based on the same criteria as those used for hair. Also, the durability of foam was evaluated based on the same criteria as those used for hair by applying model sebum to the hand. The results are shown in Table 4.

Moist Feeling
5: Very moist
4: Moist
3: Fair (equivalent to Comparative Example 2)
2: Not moist
1: Not moist at all and feels dry

TABLE 4

| Cleansing composition for skin (body shampoo) | | | Examples 50 | 51 | 52 | 53 | 54 | 55 | 56 | 57 | 58 | 59 | 60 | 61 | 62 | 63 |
|---|---|---|---|---|---|---|---|---|---|---|---|---|---|---|---|---|
| Formulation (% by mass) | (A) | Internal olefin sulfonate(3) | 12.0 | 9.6 | 9.0 | 16.0 | 4.0 | 9.6 | 9.6 | 6.0 | 9.6 | 9.6 | 9.6 | | | |
| | | Internal olefin sulfonate(4) | | 2.4 | 3.0 | 4.0 | 1.0 | 2.4 | 2.4 | 6.0 | 2.4 | 2.4 | 2.4 | | | |
| | | Internal olefin sulfonate(5) | | | | | | | | | | | | 12.0 | | |
| | | Internal olefin sulfonate(6) | | | | | | | | | | | | | 12.0 | 9.6 |
| | | Internal olefin sulfonate(7) | | | | | | | | | | | | | | 2.4 |
| | | Sodium lauryl ether sulfate *1 | | | | | | | | | | | | | | |
| | | Sodium lauryl sulfate *2 | | | | | | | | | | | | | | |
| | | Sodium α-olefin sulfonate *3 | | | | | | | | | | | | | | |
| | | Secondary alkane sulfonate *4 | | | | | | | | | | | | | | |
| | (B) | Silicone *5 | 1.0 | 1.0 | 1.0 | 1.0 | 1.0 | 0.2 | 3.0 | 1.0 | 1.0 | 1.0 | 1.0 | 1.0 | 1.0 | 1.0 |
| | | Laurie acid amide propyl betaine *6 | | | | | | | | | 2.0 | | | | | |
| | | Coconut oil fatty acid monoethanolamide *7 | | | | | | | | | | 2.0 | | | | |
| | | Lauryl glucoside *8 | | | | | | | | | | | 2.0 | | | |
| | | pH Adjuster | q.s. | | | | | | | | | | | | | |
| | | Purified water | Balance | | | | | | | | | | | | | |
| Content of internal olefin in which double bond is present at C-2 position in raw material internal olefin (% by mass) | | | 16.5 | 16.6 | 16.6 | 16.6 | 16.6 | 16.6 | 16.6 | 16.7 | 16.6 | 16.6 | 16.6 | 25.2 | 30.1 | 29.1 |
| C16/C18 Content in component (A) (% by mass) | | | 100 | 100 | 100 | 100 | 100 | 100 | 100 | 100 | 100 | 100 | 100 | 100 | 100 | 100 |
| Content of internal olefin sulfonate in which sulfonate group is present at C-2 position (% by mass) | | | 9.3 | 9.4 | 9.4 | 9.4 | 9.4 | 9.4 | 9.4 | 9.5 | 9.4 | 9.4 | 9.4 | 17.6 | 19.9 | 18.9 |
| Evaluation results | | Rinse feel | 4.2 | 4.8 | 4.8 | 4.8 | 4.4 | 4.4 | 4.4 | 4.0 | 4.4 | 4.2 | 4.2 | 4.6 | 4.2 | 4.2 |
| | | Moist feeling after towel drying | 4.0 | 4.4 | 4.4 | 4.2 | 4.2 | 3.8 | 4.4 | 4.2 | 3.8 | 4.2 | 4.0 | 4.8 | 4.0 | 4.8 |
| | | Durability of foam | — | 3.8 | — | — | — | — | — | — | — | — | — | 4.8 | 4.0 | 4.8 |

TABLE 4-continued

| Cleansing composition for skin (body shampoo) | | Examples 64 | 65 | 66 | 67 | 68 | 69 | Comparative Examples 1 | 2 | 4 | 5 | 6 | 8 | 9 | 10 |
|---|---|---|---|---|---|---|---|---|---|---|---|---|---|---|---|
| Formulation (% by mass) | (A) Internal olefin sulfonate(3) | | | | | | | | | | | | | | |
| | Internal olefin sulfonate(4) | | | | | | | | | | | | | | |
| | Internal olefin sulfonate(5) | | | | | | | | | | | | | | |
| | Internal olefin sulfonate(6) | 9.0 | 16.0 | 4.0 | 9.6 | 9.6 | 6.0 | | | | | | | | |
| | Internal olefin sulfonate(7) | 3.0 | 4.0 | 1.0 | 2.4 | 2.4 | 6.0 | | | | | | | | |
| | Sodium lauryl ether sulfate *1 | | | | | | | 12.0 | 12.0 | | | | 9.6 | 9.6 | 9.6 |
| | Sodium lauryl sulfate *2 | | | | | | | | | 12.0 | | | 2.4 | 2.4 | 2.4 |
| | Sodium α-olefin sulfonate *3 | | | | | | | | | | 12.0 | | | | |
| | Secondary alkane sulfonate *4 | | | | | | | | | | | 12.0 | | | |
| | (B) Silicone *5 | 1.0 | 1.0 | 1.0 | 0.2 | 3.0 | 1.0 | | 1.0 | 1.0 | 1.0 | 1.0 | 1.0 | 1.0 | 1.0 |
| | Laurie acid amide propyl betaine *6 | | | | | | | | | | | | 2.0 | | |
| | Coconut oil fatty acid monoethanolamide *7 | | | | | | | | | | | | | 2.0 | |
| | Lauryl glucoside *8 | | | | | | | | | | | | | | 2.0 |
| | pH Adjuster | | | | | | | q.s. | | | | | | | |
| | Purified water | | | | | | | Balance | | | | | | | |
| | Content of internal olefin in which double bond is present at C-2 position in raw material internal olefin (% by mass) | 28.8 | 29.1 | 29.1 | 29.1 | 29.1 | 27.6 | | | | | | | | |
| | C16/C18 Content in component (A) (% by mass) | 100 | 100 | 100 | 100 | 100 | 100 | | | | | | | | |
| | Content of internal olefin sulfonate in which sulfonate group is present at C-2 position (% by mass) | 18.7 | 18.9 | 18.9 | 18.9 | 18.9 | 17.5 | | | | | | | | |
| Evaluation results | Rinse feel | 4.2 | 4.4 | 4.2 | 4.4 | 3.8 | 3.8 | 3.0 | 1.8 | 3.0 | 3.0 | 2.4 | 3.0 | 3.2 | 2.2 |
| | Moist feeling after towel drying | 4.8 | 4.2 | 4.6 | 4.0 | 4.4 | 4.4 | 2.0 | 3.0 | 1.8 | 2.2 | 3.0 | 3.2 | 3.6 | 3.4 |
| | Durability of foam | 4.6 | 5.0 | 4.0 | 4.8 | 4.4 | 4.0 | — | 3.0 | — | — | — | — | — | — |

*1 Trade name: EMAL 270S (active ingredient: 70%) manufactured by Kao Corporation blended in an amount of 17.14%
*2 The product of Kao Corporation, trade name: EMAL 30N-S
*3 Trade name: LIPOLAN LB-440 (active ingredient: 36%) manufactured by Lion Corporation blended in an amount of 33.33%
*4 Trade name: Mersolat (active ingredient: 70%) manufactured by Lanxess Corporation blended in an amount of 17.14%
*5 Trade name: BY22-050A (active ingredient 50%) manufactured by Dow Corning Toray Co., Ltd.
*6 Trade name: AMPHITOL 20AB (active ingredient 30%) manufactured by Kao Corporation blended in an amount of 6.67%
*7 Trade name: Amizol CME manufactured by Kawaken Fine Chemical Co., Ltd.
*8 Trade name: MYDOL 12 (active ingredient: 40%) manufactured by Kao Corporation blended in an amount of 5.00%

Example 70 (Hair Shampoo)

A hair shampoo having a composition shown below was produced as follows: Purified water, methylparaben, and a surfactant were placed in a beaker and were heated to 80° C. with stirring. After confirmation of being uniformly dissolved, the solution was cooled to 60° C. or less, and silicone was added thereto. The solution was further cooled to 45° C. or less, and a fragrance was added thereto, followed by stirring to give a uniform solution. The solution was cooled to room temperature, and the evaporated water by heating was supplemented. The solution was further stirred for 30 minutes or more. The resulting hair shampoo was evaluated as in Example 1.

| (Component) | (% by mass) |
|---|---|
| Sodium internal olefin sulfonate (3) | 10.0 |
| Sodium internal olefin sulfonate (4) | 2.5 |
| Polyoxyethylene(1) lauryl ether ammonium sulfate *1 | 2.0 |
| Lauric acid monoethanolamide | 0.8 |
| Ethylene glycol distearate *2 | 1.0 |
| Silicone *3 | 1.0 |
| Fragrance, methylparaben | q.s. |
| Purified water | Balance |
| Total | 100.0 |

-continued

*1: EMAL 170S-A (active component: 70%) manufactured by Kao Corporation was added in an amount of 2.9%.
*2: Euperlan PK-810 (active component: 20%) manufactured by Cognis Ltd. was added in an amount of 5%.
*3: Silicone BY22-050A (active component: 55%) manufactured by Dow Corning Toray Co., Ltd. was added in an amount of 1.82%.

The resulting hair shampoo had an excellent rinse feel, and had a feeling upon application having good combing property and softness of the hair after rinsing, and excellent manageability after drying.

Example 71 (Hair Shampoo)

A hair shampoo having the following composition was produced as in Example 1, and was evaluated as in Example 1.

| (Component) | (% by mass) |
|---|---|
| Sodium internal olefin sulfonate (3) | 9.6 |
| Sodium internal olefin sulfonate (4) | 2.4 |
| Coconut oil fatty acid amide propyl betaine | 1.4 |

-continued

| (Component) | (% by mass) |
|---|---|
| Coconut oil fatty acid monoethanolamide | 0.6 |
| Silicone *1 | 1.7 |
| Ethylene glycol distearate *2 | 1.0 |
| Fragrance, sodium benzoate | q.s. |
| Purified water | Balance |
| Total | 100.0 |

*1: Silicone 1785 (active component: 60%) manufactured by Dow Corning Toray Co., Ltd. was added in an amount of 2.8%.
*2: PEARL CONCENTRATE FC-1 (active component: 20%) manufactured by Kao Corporation was added in an amount of 5%.

The resulting hair shampoo had an excellent rinse feel, and had a feeling upon application having good combing property and softness of the hair after rinsing, and excellent manageability after drying.

Example 72 (Hair Shampoo)

A hair shampoo having the following composition was produced as in Example 1, and was evaluated as in Example 1.

| (Component) | (% by mass) |
|---|---|
| Sodium internal olefin sulfonate (3) | 12.0 |
| Sodium internal olefin sulfonate (4) | 3.0 |
| Betaine lauryldimethyl aminoacetate *1 | 1.1 |
| Coconut oil fatty acid monoisopropanolamide | 1.5 |
| Amino-modified silicone *2 | 0.35 |
| Fragrance, methylparaben | q.s. |
| Purified water | Balance |
| Total | 100.0 |

*1: AMPHITOL 20BS (active component: 30%) manufactured by Kao Corporation was added in an amount of 3.8%.
*2: Silicone BY22-079 (active component: 14%) manufactured by Dow Corning Toray Co., Ltd. was added in an amount of 2.5%.

The resulting hair shampoo had an excellent rinse feel, and had a feeling upon application having good combing property and softness of the hair after rinsing, and excellent manageability-after-drying.

Example 73 (Hair Shampoo)

A hair shampoo having the following composition was produced as in Example 1, and was evaluated as in Example 1.

| (Component) | (% by mass) |
|---|---|
| Sodium internal olefin sulfonate (3) | 12.0 |
| Sodium internal olefin sulfonate (4) | 3.0 |
| Coconut oil fatty acid amide propyl betaine *1 | 1.2 |
| Imidazolium betaine *2 | 0.4 |
| Coconut oil fatty acid monoethanolamide | 1.0 |
| Silicone *3 | 0.83 |
| Ethylene glycol distearate *4 | 1.0 |
| Fragrance, sodium benzoate | q.s. |
| Purified water | Balance |
| Total | 100.0 |

*1: AMPHITOL 55AB (active component: 30%) manufactured by Kao Corporation was added in an amount of 4%.
*2: AMPHITOL 20Y-B (active component: 40%) manufactured by Kao Corporation was added in an amount of 1%.
*3: Silicone BY22-050A (active component: 55%) manufactured by Dow Corning Toray Co., Ltd. was added in an amount of 1.5%.
*4: EMAL 3201M-V manufactured by Kao Corporation The resulting hair shampoo had an excellent rinse feel, and had a feeling upon application having good combing property and softness of the hair after rinsing, and excellent manageability after drying.

Example 74 (Hair Shampoo)

A hair shampoo having the following composition was produced as in Example 1, and was evaluated as in Example 1.

| (Component) | (% by mass) |
|---|---|
| Sodium internal olefin sulfonate (3) | 6.0 |
| Sodium internal olefin sulfonate (4) | 1.5 |
| Alkyl polyglucoside *1 | 14.0 |
| Coconut oil fatty acid amide propyl betaine | 3.0 |
| Polyoxyethylene-modified silicone *2 | 2.5 |
| Fragrance, methylparaben | q.s. |
| Purified water | Balance |
| Total | 100.0 |

*1: MYDOL 10 (active component: 40%) manufactured by Kao Corporation was added in an amount of 35%.
*2: Silicone KF-6012 manufactured by Shin-Etsu Chemical Co., Ltd.

The resulting hair shampoo had an excellent rinse feel, and had a feeling upon application having good combing property and softness of the hair after rinsing, and excellent manageability after drying.

Example 75 (Hair Shampoo)

A hair shampoo having the following composition was produced as in Example 1, and was evaluated as in Example

| (Component) | (% by mass) |
|---|---|
| Sodium internal olefin sulfonate (3) | 10.0 |
| Sodium internal olefin sulfonate (4) | 2.5 |
| Coconut oil fatty acid amide propyl betaine | 3.0 |
| Coconut oil fatty acid methyl ethanolamide *1 | 1.0 |
| Polyoxypropylene (3) octyl ether | 1.0 |
| Fragrance, sodium benzoate | q.s. |
| Purified water | Balance |
| Total | 100.0 |

*1: AMINON C-11S manufactured by Kao Corporation

The resulting hair shampoo had an excellent rinse feel, and had a feeling upon application having good combing property and softness of the hair after rinsing, and excellent manageability after drying.

Example 76 (Hair Shampoo)

A hair shampoo having the following composition was produced as in Example 1, and was evaluated as in Example 1.

| (Component) | (% by mass) |
|---|---|
| Sodium internal olefin sulfonate (3) | 9.6 |
| Sodium internal olefin sulfonate (4) | 2.4 |
| Polyoxyethylene alkyl ether *1 | 0.8 |
| Lauric acid hydroxysulfobetaine *2 | 2.0 |
| 1,2-Hexanediol *3 | 1.0 |
| Silicone *4 | 1.0 |
| Ethylene glycol distearate (20%) *5 | 0.6 |

-continued

| (Component) | (% by mass) |
|---|---|
| Fragrance, sodium benzoate, lactic acid (pH adjuster) | q.s. |
| Purified water | Balance |
| Total | 100 |

*1: SymMollient W/S 174306 manufactured by Symrise AG
*2: AMPHITOL 20HD (active component: 30%) manufactured by Kao Corporation was added in an amount of 6.7%.
*3: SymDiol 68 manufactured by Symrise AG
*4: DC190 Surfactant manufactured by Dow Corning Corporation
*5: Euperlan PK1200 (active component: 20%) manufactured by Cognis Ltd. was added in an amount of 3.0%.

The resulting hair shampoo had an excellent rinse feel, and had a feeling upon application having good combing property and softness of the hair after rinsing, and excellent manageability after drying.

Example 77 (Hair Shampoo)

A hair shampoo having the following composition was produced as in Example 1, and was evaluated as in Example 1.

| (Component) | (% by mass) |
|---|---|
| Sodium internal olefin sulfonate (3) | 11.2 |
| Sodium internal olefin sulfonate (4) | 2.8 |
| Coconut oil fatty acid amide propyl betaine *1 | 0.75 |
| Coconut oil fatty acid diethanolamide | 2.0 |
| Octadecyloxypropyl trimethyl ammonium chloride *2 | 0.3 |
| Quaternium-15 *3 | 0.2 |
| *Camellia* oil | 0.2 |
| Fragrance, sodium benzoate, lactic acid (pH adjuster) | q.s. |
| Purified water | Balance |
| Total | 100.0 |

*1: AMPHITOL 55AB (active component: 30%) manufactured by Kao Corporation was added in an amount of 2.5%.
*2: QUARTAMIN E-80K (active component: 45%) manufactured by Kao Corporation was added in an amount of 0.67%.
*3: Cosept 200 manufactured by HallStar Company The resulting hair shampoo had an excellent rinse feel, and had a feeling upon application having good combing property and softness of the hair after rinsing, and excellent manageability after drying.

Example 78 (Facial Cleanser)

A facial cleanser having the following composition was produced as in Example 1, and was evaluated as in evaluation of cleansing composition for skin of Example 50.

| (Component) | (% by mass) |
|---|---|
| Sodium internal olefin sulfonate (4) | 15.0 |
| Coconut oil fatty acid monoethanolamide | 2.0 |
| Highly polymerized polydimethylsiloxane *1 | 3.0 |
| Cocamidopropyl betaine | 5.0 |
| pH adjuster | q.s. |
| Purified water | Balance |
| Total | 100.0 |

*1: BY22-060 (active component: 60%) manufactured by Dow Corning Toray Co., Ltd. was added in an amount of 5%

The resulting facial cleanser had an excellent rinse feel and had a feeling upon application having an excellent moist feeling after towel drying.

Example 79 (Facial Cleanser 2)

A facial cleanser having the following composition was produced as in Example 1, and was evaluated as in evaluation of cleansing composition for skin of Example 50.

| (Component) | (% by mass) |
|---|---|
| Sodium internal olefin sulfonate (3) | 10.0 |
| Sodium internal olefin sulfonate (4) | 2.5 |
| Coconut oil fatty acid monoethanolamide | 2.0 |
| Sunflower oil | 3.0 |
| Cetyl trimethylammonium chloride *1 | 0.5 |
| Ethylene glycol distearate *2 | 1.0 |
| pH adjuster | q.s. |
| Purified water | Balance |
| Total | 100.0 |

*1: QUARTAMIN 60W (active component: 30%) manufactured by Kao Corporation was added in an amount of 1.7%.
*2: EMAL 3201M-V manufactured by Kao Corporation The resulting facial cleanser had an excellent rinse feel and had a feeling upon application having an excellent moist feeling after towel drying.

Example 80 (Body Shampoo)

A body shampoo having the following composition was produced as in Example 1, and was evaluated as in evaluation of cleansing composition for skin of Example 50.

| (Component) | (% by mass) |
|---|---|
| Sodium internal olefin sulfonate (3) | 10.0 |
| Sodium internal olefin sulfonate (4) | 2.5 |
| Polyoxypropylene (3) octyl ether | 2.0 |
| Coconut oil fatty acid amide propyl betaine | 2.0 |
| Glycerin | 3.0 |
| Fragrance, methylparaben | q.s. |
| Purified water | Balance |
| Total | 100.0 |

The resulting body shampoo had an excellent rinse feel and had a feeling upon application having an excellent moist feeling after towel drying.

Example 81 (Body Shampoo 2)

A body shampoo having the following composition was produced as in Example 1, and was evaluated as in evaluation of cleansing composition for skin of Example 50.

| (Component) | (% by mass) |
|---|---|
| Lauryl phosphate *1 | 5.0 |
| Sodium internal olefin sulfonate (3) | 10.0 |
| Sodium internal olefin sulfonate (4) | 2.5 |
| Lauryl hydroxysulfobetaine *2 | 1.5 |
| Glycerin | 1.0 |
| Sorbitol | 2.0 |
| Jojoba oil | 1.0 |

-continued

| (Component) | (% by mass) |
|---|---|
| Ethylene glycol distearate *3 | 0.6 |
| Fragrance, methylparaben | q.s. |
| Purified water | Balance |
| Total | 100.0 |

*1: PRIOLY B-650D (active component: 50%) manufactured by Kao Corporation was added in an amount of 10.0%.
*2: AMPHITOL 20HD (active component: 30%) manufactured by Kao Corporation was added in an amount of 5.0%.
*3: PEARL CONCENTRATE SA-M2 (active component: 20%) manufactured by Kao Corporation was added in an amount of 3.0%.

The resulting body shampoo had an excellent rinse feel and had a feeling upon application having an excellent moist feeling after towel drying.

Example 82 (Body Shampoo 3)

A body shampoo having the following composition was produced as in Example 1, and was evaluated as in evaluation of cleansing composition for skin of Example 50.

| (Component) | (% by mass) |
|---|---|
| Sodium internal olefin sulfonate (3) | 10.0 |
| Sodium internal olefin sulfonate (4) | 2.5 |
| Coconut oil fatty acid amide propyl betaine *1 | 3.0 |
| Coconut oil fatty acid monoethanolamide | 2.0 |
| Cetyl alcohol | 3.0 |
| Sunflower oil | 20.0 |
| Ethylene glycol distearate *2 | 1.6 |
| Fragrance, methylparaben | q.s. |
| Purified water | Balance |
| Total | 100.0 |

*1: AMPHITOL 55AB (active component: 30%) manufactured by Kao Corporation was added in an amount of 10.0%.
*2: PEARL CONCENTRATE SA-M2 (active component: 20%) manufactured by Kao Corporation was added in an amount of 8.0%.

The resulting body shampoo had an excellent rinse feel and had a feeling upon application having an excellent moist feeling after towel drying.

Example 83 (Hand Soap)

A hand soap having the following composition was produced as in Example 1, and was evaluated as in evaluation of cleansing composition for skin of Example 50.

| (Component) | (% by mass) |
|---|---|
| Sodium internal olefin sulfonate (3) | 10.0 |
| Sodium internal olefin sulfonate (4) | 2.5 |
| Coconut oil fatty acid amide propyl betaine *1 | 3.0 |
| Ethyl alcohol | 3.0 |
| Vaseline | 0.2 |
| Fragrance, methylparaben | q.s. |
| Purified water | Balance |
| Total | 100.0 |

*1: AMPHITOL 55AB (active component: 30%) manufactured by Kao Corporation was added in an amount of 10.0%.

The resulting body shampoo had an excellent rinse feel and had a feeling upon application having an excellent moist feeling after towel drying.

INDUSTRIAL APPLICABILITY

The cleansing composition for skin or hair of the present invention can be favorably used in the fields of hair shampoo, body shampoo, facial cleanser, makeup remover, and hand soap, and the like, and further, it is also favorably applicable to animals such as dogs and cats.

The invention claimed is:

1. A method for washing hair, comprising applying a cleansing composition to hair, followed by washing and then rinsing,
- wherein the cleansing composition comprises the following components (A) and (B):
- (A) an internal olefin sulfonate having 12 or more and 24 or less carbon atoms,
- (B) an oil solution having a solubility of from 0 to 1 g in 100 g of water at 20° C.,
- wherein the oil solution (B) is at least one oil solution selected from the group consisting of an ester oil, a silicone oil, an ether oil, a hydrocarbon oil, a higher alcohol, and a carboxylic acid having a hydrocarbon group having from 17 to 23 carbon atoms which may be substituted by a hydroxyl group,
- wherein a mass content ratio (AB) of the component (A) to the component (B) is from 1 to 100,
- wherein a content of the internal olefin sulfonate in which a sulfonate group is present at the C-2 position is 5% to 25% by mass,
- wherein a mass content ratio of an internal olefin sulfonate having 16 carbon atoms to an internal olefin sulfonate having 18 carbon atoms in the internal olefin sulfonate (A) is from 50/50 to 99/1, and
- wherein said internal olefin sulfonate of 12 to 24 carbon atoms has a total content of the internal olefin sulfonate having 16 carbon atoms and the internal olefin sulfonate having 18 carbon atoms of 90% by mass or more.

2. A method for washing a body, comprising applying a cleansing composition to a surface of the skin, followed by washing and then rinsing,
- wherein the cleansing composition comprises the following components (A) and (B):
- (A) an internal olefin sulfonate having 12 or more and 24 or less carbon atoms,
- (B) an oil solution having a solubility of from 0 to 1 g in 100 g of water at 20° C.,
- wherein the oil solution (B) is at least one oil solution selected from the group consisting of an ester oil, a silicone oil, an ether oil, a hydrocarbon oil, a higher alcohol, and a carboxylic acid having a hydrocarbon group having from 17 to 23 carbon atoms which may be substituted by a hydroxyl group,
- wherein a mass content ratio (AB) of the component (A) to the component (B) is from 1 to 100,
- wherein a content of the internal olefin sulfonate in which a sulfonate group is present at the C-2 position is 5% to 25% by mass,
- wherein a mass content ratio of an internal olefin sulfonate having 16 carbon atoms to an internal olefin sulfonate having 18 carbon atoms in the internal olefin sulfonate (A) is from 50/50 to 99/1, and
- wherein said internal olefin sulfonate of 12 to 24 carbon atoms has a total content of the internal olefin sulfonate having 16 carbon atoms and the internal olefin sulfonate having 18 carbon atoms of 90% by mass or more.

3. The method for washing hair of claim 1, wherein the cleansing composition is applied to hair to impart to hair combing property after rinsing and manageability after drying.

4. The method for washing a body of claim 2, wherein the cleansing composition is applied to a surface of the skin to impart moist feeling to skin.

5. The method for washing hair of claim 1, wherein the mass content ratio (A/B) of the component (A) to the component (B) is from 1 to 60.

6. The method for washing hair of claim 1, wherein the mass content ratio (A/B) of the component (A) to the component (B) is from 1 to 50.

7. The method for washing hair of claim 1, wherein the mass content ratio (A/B) of the component (A) to the component (B) is from 4 to 60.

8. The method for washing hair of claim 1, wherein the mass content ratio (A/B) of the component (A) to the component (B) is from 5 to 50.

9. The method for washing hair of claim 1, wherein the component (B) is the ester oil, and wherein the ester oil is one represented by Formula (1) or (2) shown below or a hydrophobic carboxylic acid ester of dipentaerythritol,

R1-COO—R2 (1)

wherein R1 represents a linear or branched alkyl or alkenyl group having from 8 to 22 carbon atoms; and R2 represents a linear or branched alkyl or alkenyl group having from 1 to 22 carbon atoms, (2)

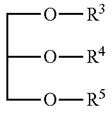

wherein R3, R4, and R5 each independently represent a hydrogen atom or a group represented by Formula (3), provided that they are not simultaneously hydrogen atoms, (3)

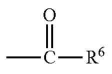

wherein R6 represents a linear or branched alkyl or alkenyl group having from 8 to 22 carbon atoms which may be substituted by a hydroxyl group.

10. The method for washing hair of claim 1, wherein the component (B) is the silicone oil, wherein the silicone oil has a viscosity of from 10 to 15,000,000 mm2/s, and wherein the silicone oil is at least one silicone oil selected from the group consisting of dimethylpolysiloxane, dimethiconol, amino modified silicone, polyether modified silicone, glyceryl modified silicone, amino derivative silicone, silicone wax, and silicone elastomer.

11. The method for washing hair of claim 1, wherein the component (B) is the hydrocarbon oil, and wherein the hydrocarbon oil is one or two or more selected from squalene, squalane, liquid paraffin, liquid isoparaffin, heavy liquid isoparaffin, α-olefin oligomer, cycloparaffin, polybutene, petroleum jelly, paraffin wax, microcrystalline wax, polyethylene wax, and ceresin.

12. The method for washing hair of claim 1, wherein the component (B) is the higher alcohol, wherein the higher alcohol is an alcohol having a linear or branched alkyl group or alkenyl group having from 6 to 22 carbon atoms, and wherein the higher alcohol is at least one higher alcohol selected from the group consisting of hexyl alcohol, 2-ethylhexyl alcohol, octyl alcohol, decyl alcohol, isodecyl alcohol, lauryl alcohol, myristyl alcohol, palmityl alcohol, cetyl alcohol, stearyl alcohol, isostearyl alcohol, 2-octyl dodecanol, icosyl alcohol, and behenyl alcohol.

13. The method for washing hair of claim 1, wherein the component (B) is the carboxylic acid having a hydrocarbon group having from 17 to 23 carbon atoms which may be substituted by a hydroxyl group, and wherein the carboxylic acid having a hydrocarbon group having from 17 to 23 carbon atoms which may be substituted by a hydroxyl group is one or two or more selected from stearic acid, oleic acid, isostearic acid, hydroxystearic acid, behenic acid, and rosin acid.

14. The method for washing a body of claim 2, wherein the mass content ratio (A/B) of the component (A) to the component (B) is from 1 to 60.

15. The method for washing a body of claim 2, wherein the mass content ratio (A/B) of the component (A) to the component (B) is from 1 to 50.

16. The method for washing a body of claim 2, wherein the mass content ratio (A/B) of the component (A) to the component (B) is from 4 to 60.

17. The method for washing a body of claim 2, wherein the mass content ratio (A/B) of the component (A) to the component (B) is from 5 to 50.

18. The method for washing a body of claim 2, wherein the component (B) is the ester oil, and wherein the ester oil is one represented by Formula (1) or (2) shown below or a hydrophobic carboxylic acid ester of dipentaerythritol,

R1-COO—R2 (1)

wherein R1 represents a linear or branched alkyl or alkenyl group having from 8 to 22 carbon atoms; and R2 represents a linear or branched alkyl or alkenyl group having from 1 to 22 carbon atoms, (2)

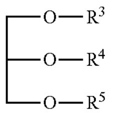

wherein R3, R4, and R5 each independently represent a hydrogen atom or a group represented by Formula (3), provided that they are not simultaneously hydrogen atoms, (3)

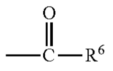

wherein R6 represents a linear or branched alkyl or alkenyl group having from 8 to 22 carbon atoms which may be substituted by a hydroxyl group.

19. The method for washing body of claim 2, wherein the component (B) is the silicone oil, wherein the silicone oil is at least one silicone oil selected from the group consisting of dimethylpolysiloxane, dimethiconol, amino modified silicone, polyether modified silicone, glyceryl modified silicone, amino derivative silicone, silicone wax, and silicone elastomer.

20. The method for washing body of claim 2, wherein the component (B) is the hydrocarbon oil, and wherein the hydrocarbon oil is at least one hydrocarbon oil selected from the group consisting of squalene, squalane, liquid paraffin, liquid isoparaffin, heavy liquid isoparaffin, α-olefin oligomer, cycloparaffin, polybutene, petroleum jelly, paraffin wax, microcrystalline wax, polyethylene wax, and ceresin.

21. The method for washing body of claim 2, wherein the component (B) is the higher alcohol, wherein the higher alcohol is an alcohol having a linear or branched alkyl group or alkenyl group having from 6 to 22 carbon atoms, and wherein the higher alcohol is at least one higher alcohol selected from the group consisting of hexyl alcohol, 2-ethylhexyl alcohol, octyl alcohol, decyl alcohol, isodecyl alcohol, lauryl alcohol, myristyl alcohol, palmityl alcohol, cetyl alcohol, stearyl alcohol, isostearyl alcohol, 2-octyl dodecanol, icosyl alcohol, and behenyl alcohol.

22. The method for washing body of claim 2, wherein the component (B) is the carboxylic acid having a hydrocarbon group having from 17 to 23 carbon atoms which may be substituted by a hydroxyl group, and wherein the carboxylic acid having a hydrocarbon group having from 17 to 23 carbon atoms which may be substituted by a hydroxyl group is at least one carboxylic acid selected from the group consisting of stearic acid, oleic acid, isostearic acid, hydroxystearic acid, behenic acid, and rosin acid.

23. The method for washing hair of claim 1, wherein the content mass ratio of the internal olefin sulfonate having 16 carbon atoms to the internal olefin sulfonate having 18 carbon atoms is from 70/30 to 90/10.

24. The method for washing a body of claim 2, wherein the content mass ratio of the internal olefin sulfonate having 16 carbon atoms to the internal olefin sulfonate having 18 carbon atoms is from 70/30 to 90/10.

* * * * *